United States Patent
Muse et al.

(10) Patent No.: US 12,327,637 B2
(45) Date of Patent: Jun. 10, 2025

(54) SEIZURE PREDICTION MACHINE LEARNING MODELS

(71) Applicant: OPTUM, INC., Minnetonka, MN (US)

(72) Inventors: Jon Kevin Muse, Thompsons Station, TN (US); Gregory J. Boss, Saginaw, MI (US); Yash Sharma, Noida (IN); Komal Khatri, Cedar Park, TX (US)

(73) Assignee: OPTUM, INC., Minnetonka, MN (US)

( * ) Notice: Subject to any disclaimer, the term of this patent is extended or adjusted under 35 U.S.C. 154(b) by 354 days.

(21) Appl. No.: 17/451,729

(22) Filed: Oct. 21, 2021

(65) Prior Publication Data

US 2023/0128944 A1    Apr. 27, 2023

(51) Int. Cl.
| | |
|---|---|
| *G16H 50/20* | (2018.01) |
| *G02C 7/10* | (2006.01) |
| *G06V 40/16* | (2022.01) |
| *G16H 15/00* | (2018.01) |
| *G16H 40/67* | (2018.01) |

(52) U.S. Cl.
CPC ............ *G16H 50/20* (2018.01); *G02C 7/101* (2013.01); *G06V 40/176* (2022.01); *G16H 15/00* (2018.01); *G16H 40/67* (2018.01)

(58) Field of Classification Search
CPC ........ G16H 50/20; G16H 15/00; G16H 40/67; G06V 40/176
See application file for complete search history.

(56) References Cited

U.S. PATENT DOCUMENTS

| | | | |
|---|---|---|---|
| 5,552,841 A | 9/1996 | Gallorini et al. | |
| 8,752,963 B2 | 6/2014 | McCulloch et al. | |
| 10,336,256 B1 | 7/2019 | Pertsel et al. | |
| 10,444,505 B2 | 10/2019 | Rousseau et al. | |
| 10,742,923 B2 | 8/2020 | Rechner et al. | |
| 10,795,184 B2 | 10/2020 | Antaki et al. | |
| 10,955,917 B2 * | 3/2021 | Ramaprakash | G06T 11/60 |
| 2016/0170206 A1 * | 6/2016 | Osborne | G02B 27/017 |
| | | | 345/8 |
| 2019/0336061 A1 * | 11/2019 | Harrer | A61B 5/7275 |
| 2021/0199966 A1 * | 7/2021 | Huang | G02B 6/005 |
| 2021/0259621 A1 * | 8/2021 | Alves | A61B 5/4094 |
| 2021/0282701 A1 * | 9/2021 | Chan | A61B 5/37 |

(Continued)

FOREIGN PATENT DOCUMENTS

WO    1997/022904 A1    6/1997

OTHER PUBLICATIONS

Begley, Charles E. et al. "The Direct Cost of Epilepsy In The United States: A Systematic Review of Estimates," Epilepsia, Jul. 27, 2015, vol. 56, No. 9, pp. 1376-1387, DOI: 10.1111/epi.13084.

(Continued)

*Primary Examiner* — Robert A Sorey
*Assistant Examiner* — Kristine K Rapillo
(74) *Attorney, Agent, or Firm* — Alston & Bird LLP

(57) ABSTRACT

Various embodiments of the present disclosure provide methods, apparatuses, systems, computing devices, computing entities, and/or the like for detecting and preventing seizure events in real-time. For example, various embodiments provide techniques for detecting and preventing seizure events in real-time that use seizure prediction machine learning models.

20 Claims, 10 Drawing Sheets

(56) References Cited

U.S. PATENT DOCUMENTS

2022/0061678 A1* 3/2022 Schulhauser ........ A61B 5/6803
2022/0148713 A1* 5/2022 Gordon .................. G16H 30/40

OTHER PUBLICATIONS

Lee, Sang-Mok et al. "Highly Transparent, Deformable, and Multifunctional AgPdCu/ITO/PTFE Hybrid Films for Self-Cleaning, Flexible, and Energy-Saving Smart Windows," Advanced Materials Interfaces, vol. 5, No. 22:1801082. Sep. 19, 2018, DOI: 10.1002/admi.201801082.

Runji, Joel Murithi et al. "Switchable Glass Enabled Contextualization For A Cyber-Physical Safe and Interactive Spatial Augmented Reality PCBA Manufacturing Inspection System," Sensors, vol. 20, No. 15:4286, Jan. 2020, pp. 1-25, DOI: 10.3390/s20154286.

"Epilepsy Fast Facts,"Centers For Disease Control and Prevention, Sep. 30, 2020, (2 pages), (online), [Retrieved from the Internet Feb. 19, 2022] <URL: https://www.cdc.gov/epilepsy/about/fast-facts.htm#:~:2text=Active%20Epilepsy&text=This%20is%20about%203.4%20million,million%20adults%20and%20470%2C000%20children.&text=According%20to%20the%20latest%20estimates,17%20years%20have%20active%20epilepsy.&text=Think%20of%20a%20school%20with,of%20them%.

"Epilepsy," World Health Organization, Feb. 9, 2022, (5 pages), (online), [Retrieved from the Internet Feb. 19, 2022] <URL: https://www.who.int/news-room/fact-sheets/detail/epilepsy#:~:text=Around%2050%20million%20people%20worldwide%20have%20epilepsy%2C%20making%20it%20one,if%20properly%20diagnosed%20and%20treated>.

"Examining The Economic Impact and Implications of Epilepsy," The American Journal of Managed Care, Feb. 13, 2020, (7 pages), (article, online), [Retrieved from the Internet Feb. 19, 2022] <URL: https://www.ajmc.com/view/examining-the-economic-impact-and-implications-of-epilepsy>.

"Polymer Dispersed Liquid Crystal," PDLC|Q-sys, (3 pages), (article, online), [Retrieved from the Internet Feb. 19, 2022] <URL: http://www.q-sys.co.kr/en/bbs/content.php?co_id=en_tech1&device=mobile>.

\* cited by examiner

SEIZURE PREDICTION MACHINE LEARNING MODELS

BACKGROUND

Various individuals may be prone to seizures which can lead to serious and sometimes fatal injuries. Through applied effort, ingenuity, and innovation, various apparatuses, systems, and methods have been realized for detecting and/or preventing seizures in order to decrease a person's risk of injury.

BRIEF SUMMARY

In general, various embodiments of the present disclosure provide methods, apparatuses, systems, computing devices, computing entities, and/or the like for detecting and preventing seizure events in real-time. For example, various embodiments provide techniques for detecting and preventing seizure events in real-time that use seizure prediction machine learning models.

In accordance with one aspect, a method is provided. In one embodiment, the method comprises: identifying, based at least in part on the event data object, one or more predefined head movement features and one or more predefined facial movement features associated with a user, wherein the event data object comprises sensor data associated with: (i) the user's face, (ii) the user's head movements, and (iii) the user's field of view; determining, using a seizure prediction machine learning model, the seizure event prediction, wherein the seizure event prediction comprises a seizure event type that is determined based at least in part on the one or more predefined head movement features and the one or more predefined facial movement features; and performing one or more prediction-based tasks based at least in part on the seizure event prediction.

In accordance with another aspect, a computer program product is provided. The computer program product may comprise at least one computer-readable storage medium having computer-readable program code portions stored therein, the computer-readable program code portions comprising executable portions configured to: identify, based at least in part on the event data object, one or more predefined head movement features and one or more predefined facial movement features associated with a user, wherein the event data object comprises sensor data associated with: (i) the user's face, (ii) the user's head movements, and (iii) the user's field of view; determine, using a seizure prediction machine learning model, the seizure event prediction, wherein the seizure event prediction comprises a seizure event type that is determined based at least in part on the one or more predefined head movement features and the one or more predefined facial movement features; and perform one or more prediction-based tasks based at least in part on the seizure event prediction.

In accordance with yet another aspect, an apparatus comprising at least one processor and at least one memory including computer program code is provided. In one embodiment, the at least one memory and the computer program code may be configured to, with the processor, cause the apparatus to: identify, based at least in part on the event data object, one or more predefined head movement features and one or more predefined facial movement features associated with a user, wherein the event data object comprises sensor data associated with: (i) the user's face, (ii) the user's head movements, and (iii) the user's field of view; determine, using a seizure prediction machine learning model, the seizure event prediction, wherein the seizure event prediction comprises a seizure event type that is determined based at least in part on the one or more predefined head movement features and the one or more predefined facial movement features; and perform one or more prediction-based tasks based at least in part on the seizure event prediction.

BRIEF DESCRIPTION OF THE DRAWINGS

Figure 1:
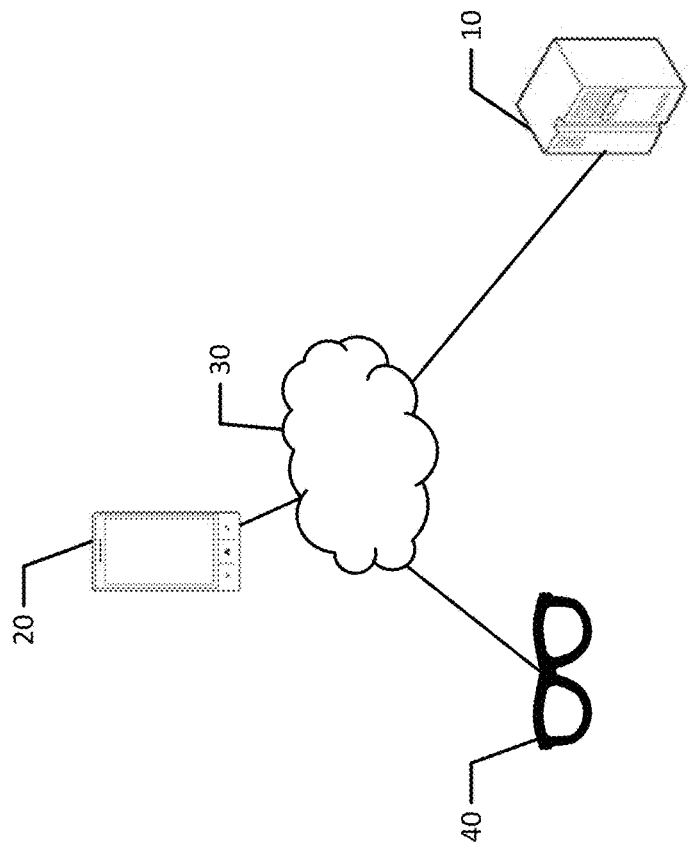
Figure 2:
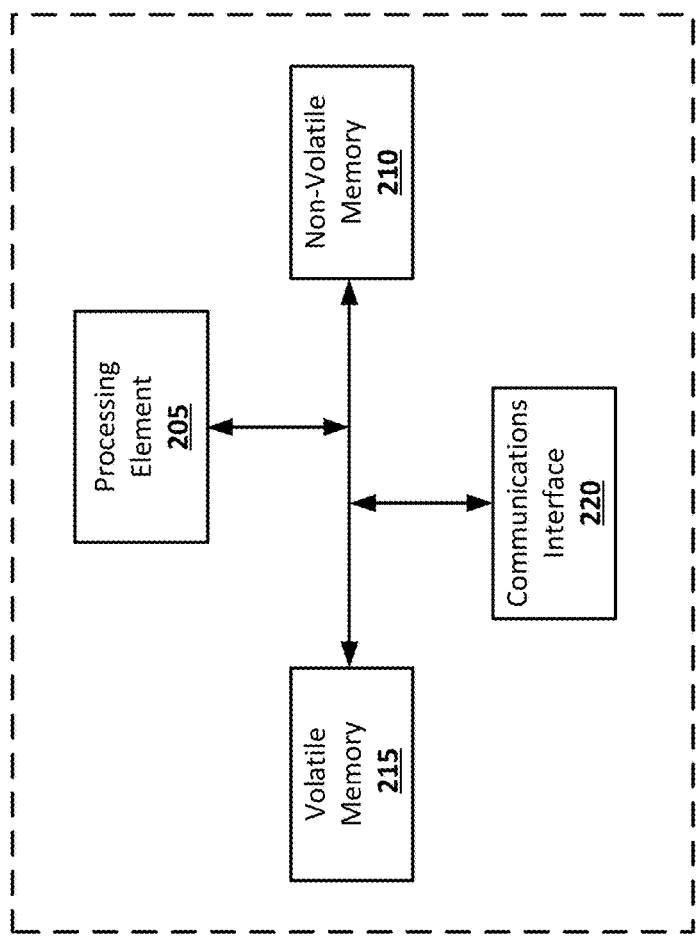
Figure 3:
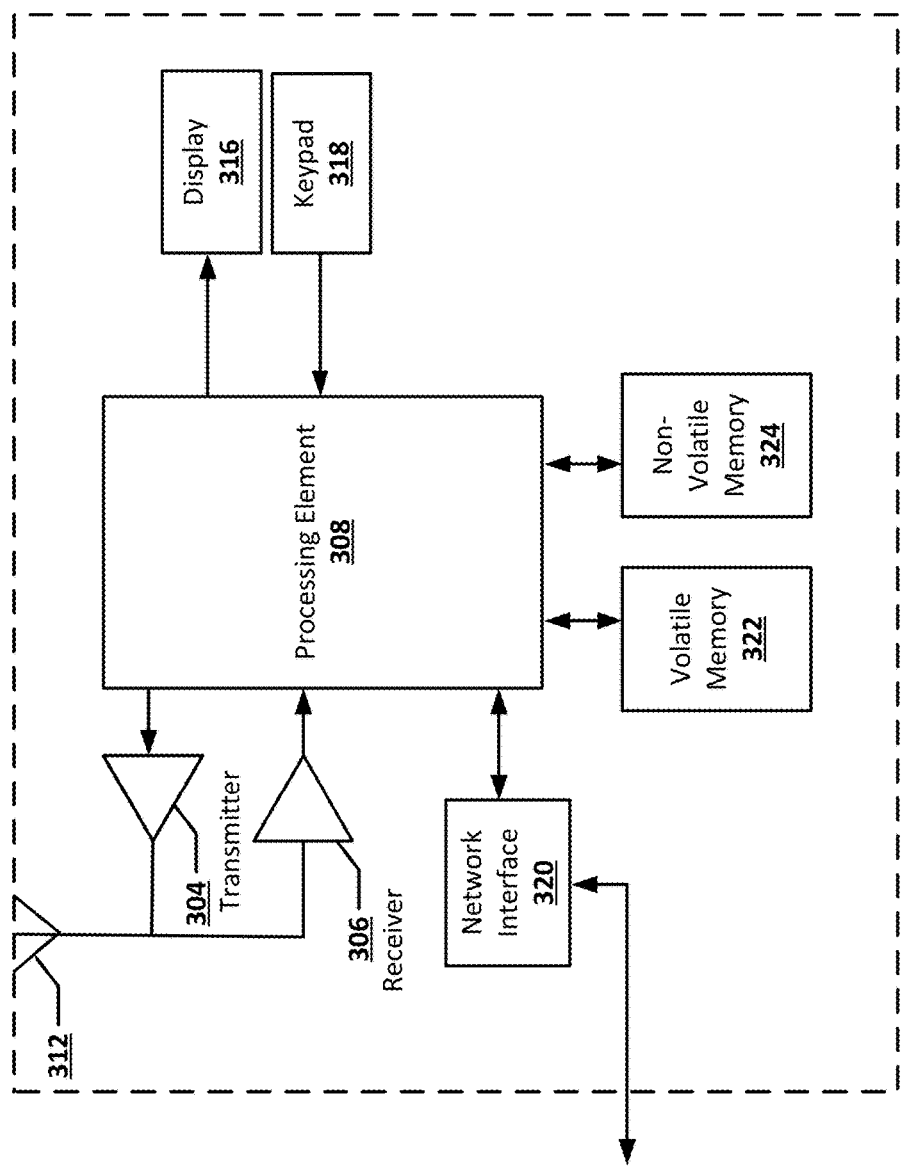
Figure 4:
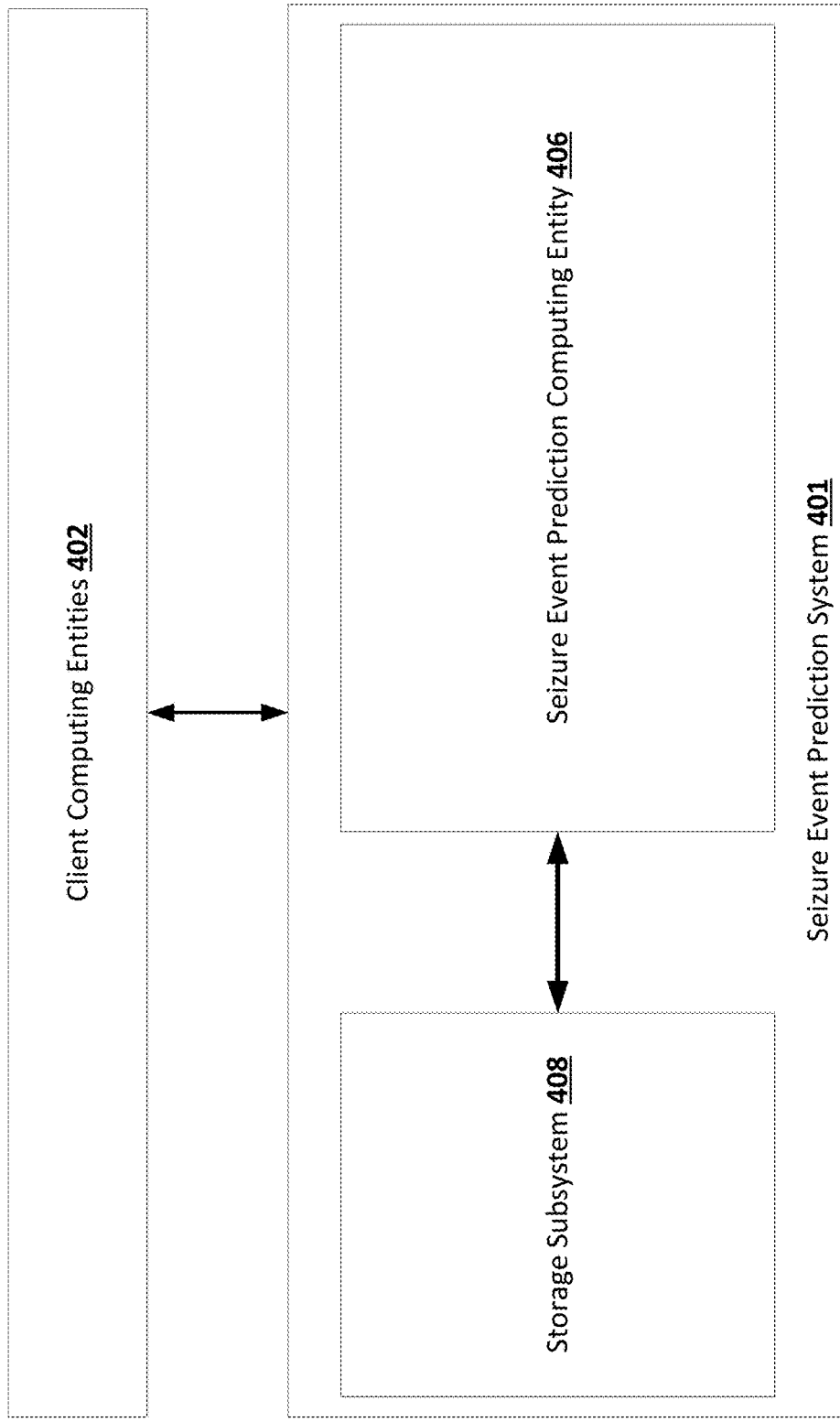
Figure 5:
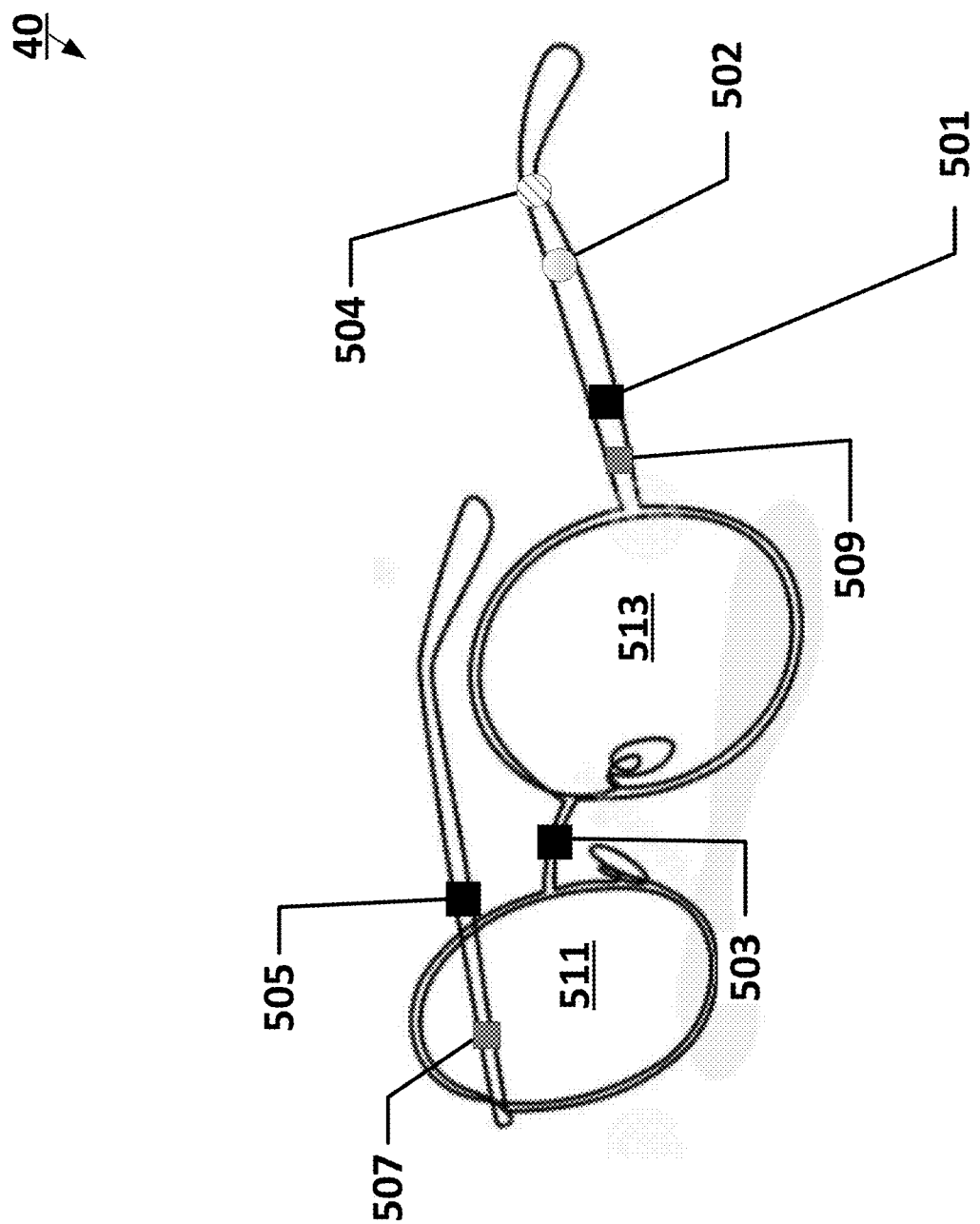
Figure 6:
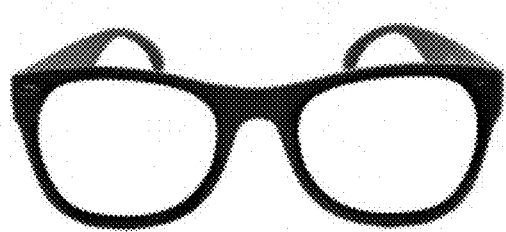
Figure 6:
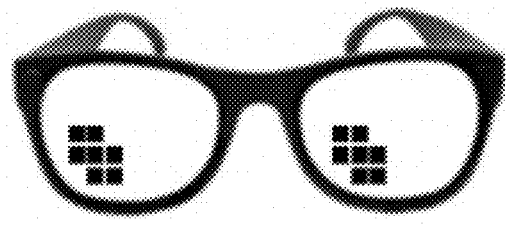
Figure 7:
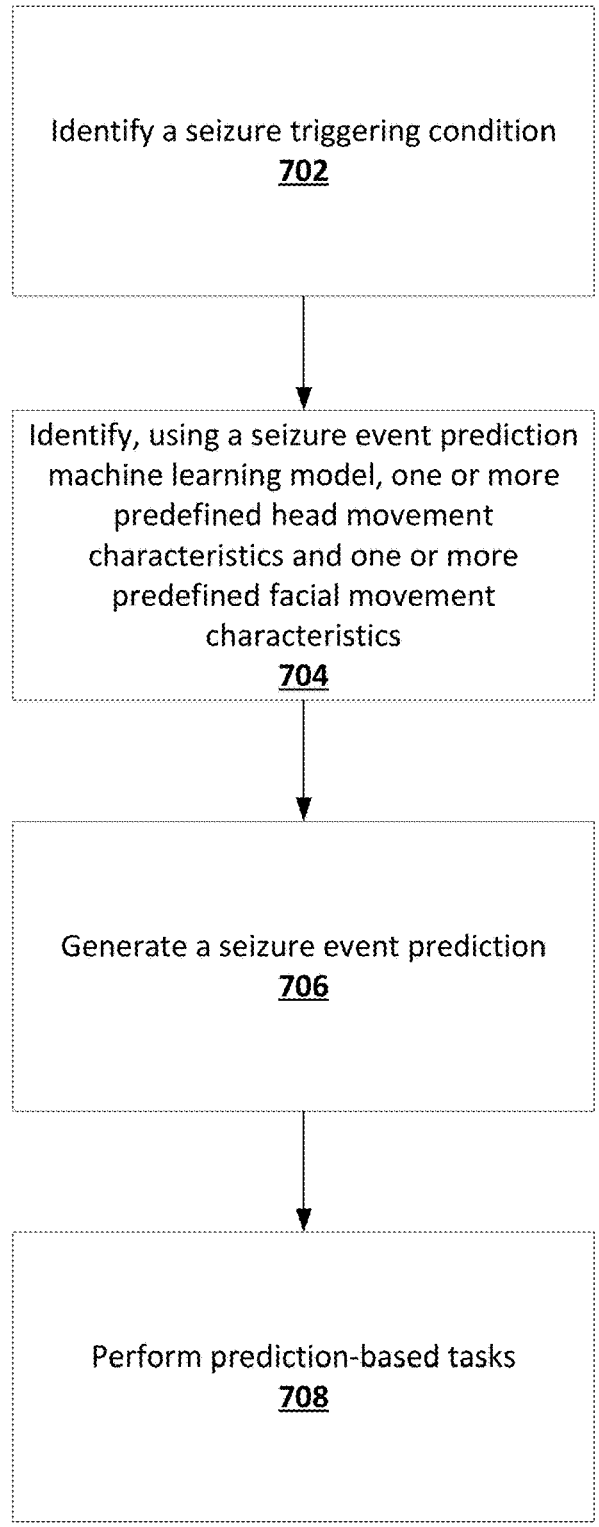
Figure 8:
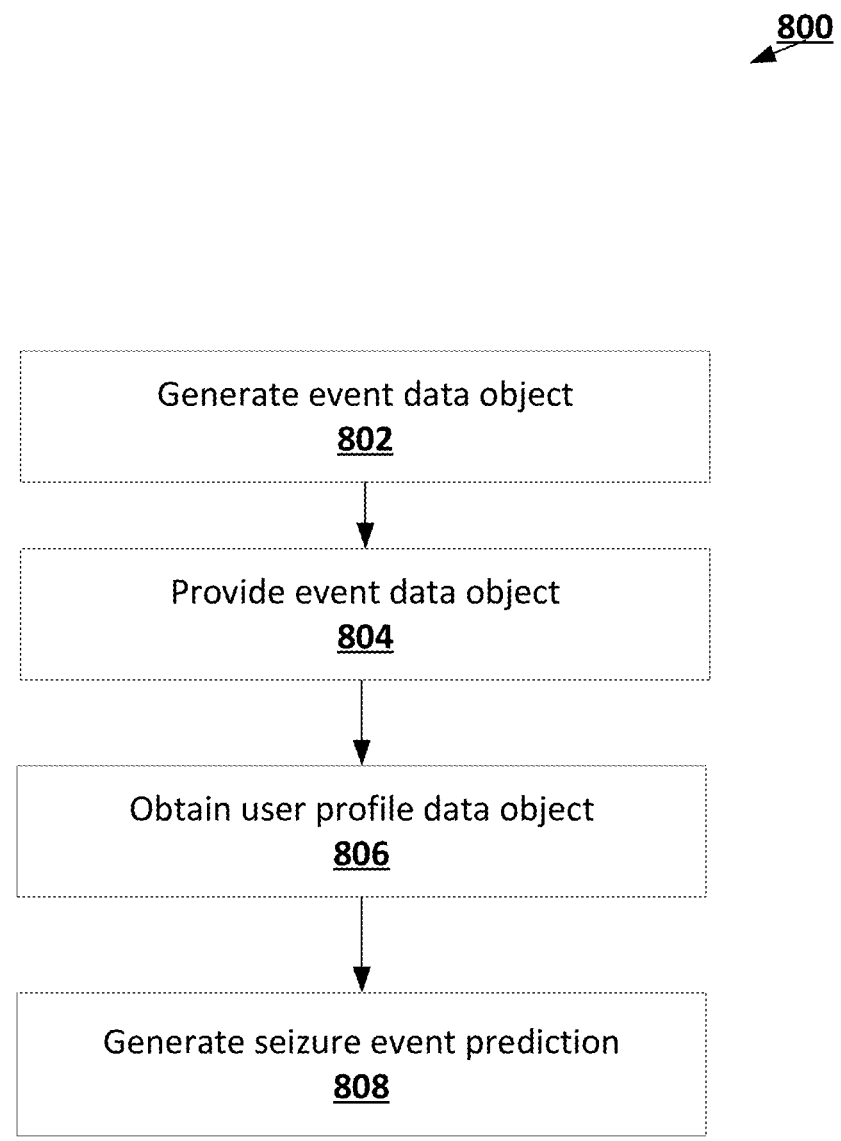
Figure 9:
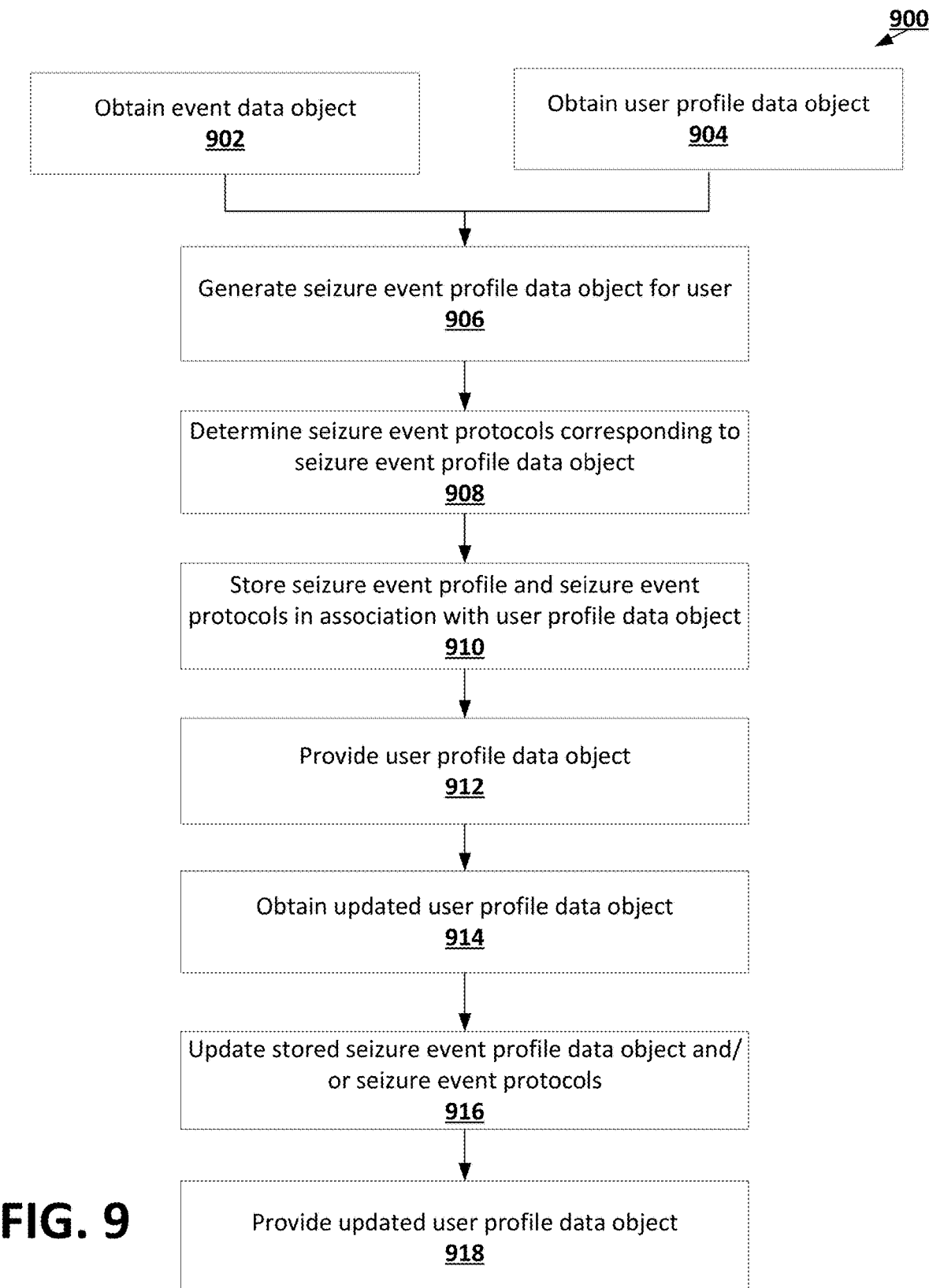
Figure 10:
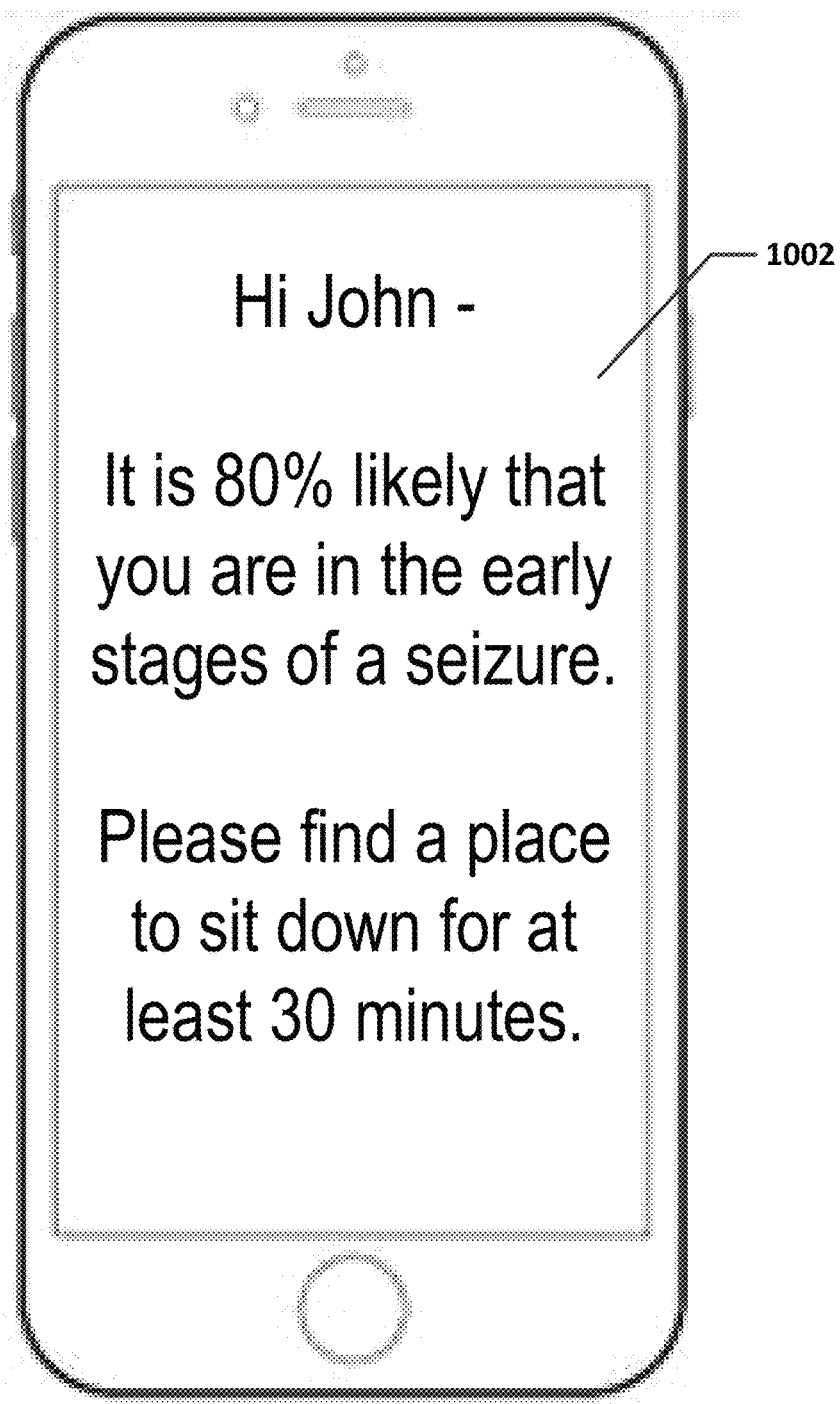

Having thus described the invention in general terms, reference will now be made to the accompanying drawings, which are not necessarily drawn to scale, and wherein:

FIG. 1 is an exemplary overview of a system architecture that can be used to practice various embodiments of the present disclosure;

FIG. 2 is an example schematic of a seizure event prediction computing entity in accordance with certain embodiments of the present disclosure;

FIG. 3 is an example schematic of a user computing entity in accordance with certain embodiments of the present disclosure;

FIG. 4 is an example schematic of a seizure event prediction system in accordance with certain embodiments of the present disclosure;

FIG. 5 is an example schematic depicting a wearable device, in accordance with certain embodiments of the present disclosure;

FIG. 6 is an operational example depicting opacity changes, in accordance with certain embodiments of the present disclosure;

FIG. 7 is a flowchart diagram illustrating an example process for generating a seizure event prediction;

FIG. 8 is a flowchart diagram illustrating an example process for identifying a seizure event, in accordance with certain embodiments of the present disclosure;

FIG. 9 is a flowchart diagram illustrating an example process for updating a user profile data object, in accordance with certain embodiments of the present disclosure; and FIG. 10 is an example view of a user interface, in accordance with certain embodiments of the present disclosure.

DETAILED DESCRIPTION

Various embodiments of the present disclosure now will be described more fully hereinafter with reference to the accompanying drawings, in which some, but not all embodiments are shown. Indeed, various configurations as discussed herein may be embodied in many different forms and should not be construed as limited to the embodiments set forth herein; rather, these embodiments are provided so that this disclosure will satisfy applicable legal requirements. The term "or" (also designated as "/") is used herein in both the alternative and conjunctive sense, unless otherwise indicated. The terms "illustrative" and "exemplary" are used to be examples with no indication of quality level. Like numbers refer to like elements throughout.

I. Overview

Various embodiments are directed to systems, apparatuses, and/or methods for detecting, preventing and mitigating seizure events. Additionally, there is a need for systems and techniques for obtaining, analyzing and providing data associated with seizure events in order to prevent future events that can account for individual user features and requirements including user response to interventions over time.

Various embodiments of the present disclosure are directed to a wearable device (e.g., glasses or spectacles) having an integrated controller and one or more sensors that are collectively configured to detect potential and actual seizure events and, in some examples, initiate a seizure response protocol. In some embodiments, based at least in part on detecting a seizure triggering condition, the controller may provide a control indication to cause opacity changes to at least one surface (e.g., lenses) of the wearable device. In some embodiments, based at least in part on an identified seizure triggering condition, head movement features and/or facial movement features, a corresponding seizure response protocol may be identified and initiated. A seizure response protocol may be dynamically adjusted (e.g., in real-time) based at least in part on user input and/or by monitoring user response. Additionally, the user seizure profile of a user may be refined over time using machine learning techniques to identify optimal parameters for seizure response protocols and more accurately detect different types of seizure events. To further enhance system performance, the wearable device may be calibrated based at least in part on user features (e.g., age, gender, biometric information, and/or the like), and any changes thereto.

The apparatuses, systems, and methods described herein provide a robust seizure event detection and prevention system. Moreover, various embodiments of the present invention disclose seizure prediction machine learning models that can make inferences based on sensory data in order to perform seizure event/seizure event type detection in a more computationally manner compared to the state-of-the-art systems. Accordingly, various embodiments of the present disclosure make substantial technical contributions to the field of monitoring devices and substantially improve state-of-the-art systems.

II. Definitions of Certain Terms

The term "body" may refer to a person's physical form, and the term may specifically be utilized to refer to a portion of a person's body, including at least a portion of one or more internal and/or external organs of a user. In general, the terms user, patient, wearer, individual, person and/or similar words are used herein interchangeably.

The term "electronically coupled" or "in electronic communication with" may refer to two or more electrical elements (for example, but not limited to, an example processing circuitry, communication module, input/output module memory, pulse wave generator, electrodes) and/or electric circuit(s) being connected through wired means (for example but not limited to, conductive wires or traces) and/or wireless means (for example but not limited to, wireless network, electromagnetic field), such that data and/or information (for example, electronic indications, signals) may be transmitted to and/or received from the electrical elements and/or electric circuit(s) that are electronically coupled.

The term "seizure" or "seizure event" may refer to an event or state of a person in which abnormal nerve cell and/or electrical activity in the brain induces one or more physical symptoms including, for example, rhythmic muscular contractions (e.g., convulsions), fainting, fatigue, paralysis, loss of bladder control, headaches and/or the like. A seizure may comprise a plurality of different stages. By way of example, certain seizures may comprise a prodrome stage, an aura stage (early ictal stage), an ictal stage and a postictal stage. During the prodrome stage, a person may experience changes in mood or behavior including anxiety, irritability and/or lightheadedness. During the aura/early ictal stage, the person may experience subtle twitching in his or her arms or legs, changes in smell, taste, vision and perception. The ictal stage may be characterized by more visible/serious seizure activity (e.g., twitching, jerking, convulsions or the like) lip smacking, chewing, loss of consciousness, heart racing, sweating, tremors, pupil dilation, and/or the like. During the postictal stage, the seizure may subside and the person may experience confusion, drowsiness, weakness and/or disorientation.

The term "pre-seizure event" may refer to the prodrome and/or aura stages of a seizure where subtle/early signs or indications of a seizure are present. In particular, the pre-seizure event can be associated with a combination of detectable and/or non-detectable symptoms including slight twitching of the body (e.g., eyes, face, head, arms and/or legs), changes in taste, dizziness, vision changes, body pain, nausea, and/or the like.

The term "wearable device" may refer to an electronic device that is configured to be worn proximate or adjacent a wearer's head and/or face. In some embodiments, the wearable device can be embodied as eyewear (e.g., spectacles, glasses or the like) configured to be worn over or adjacent the wearer's eyes. In such embodiments, the wearable device may comprise at least one transparent surface (e.g., lenses) that is capable of exhibiting opacity changes in response receiving a control indication. In some embodiments, the at least one transparent surface may comprise a Polymer Dispersed Liquid Crystal (PLDC) film. Additionally, the example wearable device may comprise one or more sensors such as inertial measurement units (IMUs), image sensors (e.g., cameras), accelerometers, gyroscopes, combinations thereof, and/or the like. In some embodiments, a wearable device may be embodied as a hat, cap, face shield, visor, headphones, earphones, an earpiece, a watch, combinations thereof, and/or the like. In some embodiments, the wearable device can be embodied as a car windshield or window proximate a user. Such alternative example wearable devices may include or be in electronic communication with at least one transparent surface disposed adjacent the wearer's eyes and/or face. In various embodiments, an example wearable device may comprise at least a power source (e.g., a rechargeable battery), a controller or processor and a wireless communication transceiver.

The term "sensor data" may refer to physiological information/data, biometric information/data, accelerometer information/data, location information/data, environmental information/data, image/video sensor information/data, and/or the like which may be associated with a particular person (e.g., a user of a wearable device). Sensor data may be collected and/or generated by one or more sensors associated with the user, such as mobile device sensors, wearable device sensors, sensors associated with one or more devices commonly used by the user (e.g., a glucose monitoring device), and/or the like. In some examples, embodiments, the sensor data may include image data, muscle condition data, heart rate data, oxygen saturation data, pulse rate data, body temperature data, breath rate data, perspiration data, blink rate data, blood pressure data, neural activity data, cardiovascular data, pulmonary data, and/or various other types of information/data. In some embodiments, sensor data may be stored in conjunction with a user profile.

The term "seizure triggering condition" may refer to a data object that is configured to describe one or more detected visual features within a person's field of view that can trigger a seizure. By way of example, a seizure triggering condition may comprise an object, visual pattern, intensity of light, strobing light, changing color profiles, irregular geometric shape(s), and/or the like in the person's field of view.

The term "seizure event prediction machine learning model" may refer to a data object that describes steps/operations, hyper-parameters, and/or parameters of a machine learning model/algorithm that is configured to generate data needed to infer/generate a seizure event prediction with respect to a person (e.g., a user of a wearable device). The steps/operations of the seizure event prediction machine learning model may lead to performing one or more prediction-based tasks (e.g., triggering a seizure response protocol). In some embodiments, the seizure event prediction machine learning model may comprise a first sub-model that is configured to identify a seizure triggering condition in a user's field of view. In some embodiments, the seizure event prediction machine learning model may comprise a second sub-model that is configured to identify one or more predefined head movement features and one or more predefined facial movement features associated with a user's head movements and facial movements. In some embodiments, the predefined head movement features may comprise three dimensional head rotations and/or accelerations. In some embodiments, the predefined facial movement features may comprise rhythmic eye movements, a fixed gaze for a predefined length of time, repetitive vibrations of any portion of the face, a tasting gesture and a pupil size or change in pupil size. In some embodiments, the second-sub-model of the seizure event prediction machine learning model may identify the one or more head movement features and one or more facial movement features using a Eulerian video processing technique. The seizure event prediction machine learning model may be trained based at least in part on a ground truth seizure event. By way of example, the seizure event prediction machine learning model/algorithm may be a neural network, a convolutional neural network (CNN), a recurrent neural network (RNN), and/or the like.

The term "seizure event prediction" may refer to a data object that describes a predictive output of one or more computer-implemented processes, wherein the predictive output describes one or more predictive inferences such as an inferred determination relating to whether or not a person is experiencing or is likely to experience a seizure. In some embodiments, determining a seizure event prediction may comprise processing an event data object describing sensor data associated with a user of a wearable device. In some embodiments, the seizure event prediction may be an output of the seizure event prediction machine learning model. Additionally, in some embodiments, determining the seizure event prediction may comprise identifying a seizure type or phase. Determining the seizure event prediction may comprise identifying a seizure triggering condition in a user's field of view, one or more head movement features, and/or one or more facial movement features from an event data object. In some examples, the seizure event prediction may be a value (e.g., a percentage value or a number between 0 and 1), where an above-threshold value indicates that a person (e.g., a user of a wearable device) is experiencing or likely to experience a seizure event.

The term "event data object" may refer to a data object storing and/or providing access to information/data that is related to a user of a wearable device. In some embodiments, an event data object may describe one or more recorded events associated with a user of a wearable device. In some embodiments, the event data object may comprise sensor data (e.g., image data, acceleration data and/or the like) associated with one or more of the user's face, the user's head movements, and the user's field of view. In some embodiments, an event data object may comprise audio information/data, image/video sensor information/data, physiological information/data, biometric information/data, accelerometer information/data, location information/data, environmental information/data, combinations thereof, and/or the like.

The term "Eulerian video processing (EVP) technique" may refer to a data object that describes step/operations of a spatial-temporal video processing algorithm that is configured to process an input video sequence comprising a plurality of frames (e.g., a plurality of consecutive image frames that collectively define a video) by applying spatial decomposition and temporal filtering in order to reconstruct the plurality of frames. The resulting signal is then amplified to emphasize spatial changes between images/objects within frames, facilitating visualization of otherwise imperceptible/minute changes of motion captured in the frames. The output video sequence of the EVP technique reveals features at selected temporal frequencies that are imperceptible in the unprocessed input video sequence. Accordingly, the EVP technique may be utilized to identify one or more head movement features and/or facial movement features associated with a user. For example, the output of an EVP technique executed for an input video sequence depicting a portion of a user's face may reveal eye twitching and/or facial muscular movements that are imperceptible in the unprocessed input video sequence.

The term "seizure response protocol" may refer to a data object that describes one or more recommended actions (e.g., a particular set or sequence of actions) that are associated with a seizure event prediction (e.g., an identified seizure event or a predicted seizure event). In some embodiments, a seizure response protocol may be associated with a particular seizure event type. A seizure response protocol may be triggered/initiated in response to generating a predicted seizure event (e.g., identifying a seizure event type). In some embodiments, the seizure response protocol may comprise one or more of providing an audio alert, transmitting a notification or alert (e.g., to another computing entity, for display to a person, to onlookers in a person's vicinity), obtaining additional sensor data (e.g., via one or more sensors of a wearable device and/or other computing entity (e.g., mobile device, smartwatch or the like)), generating and providing a report of a seizure event, and/or the like.

III. Computer Program Products, Methods, and Computing Devices

Embodiments of the present disclosure may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In some embodiments, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In some embodiments, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present disclosure may also be implemented as methods, apparatus, systems, computing devices, computing entities, and/or the like. As such, embodiments of the present disclosure may take the form of a data structure, apparatus, system, computing device, computing entity, and/or the like executing instructions stored on a computer-readable storage medium to perform certain steps or operations. Thus, embodiments of the present disclosure may also take the form of an entirely hardware embodiment, an entirely computer program product embodiment, and/or an embodiment that comprises combination of computer program products and hardware performing certain steps or operations.

Embodiments of the present disclosure are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. Exemplary System Architecture

FIG. 1 provides an example system architecture 100 that can be used in conjunction with various embodiments of the present disclosure. As shown in FIG. 1, the system architecture 100 may comprise one or more seizure event prediction computing entities 10, one or more user computing entities 20, one or more networks 30, one or more wearable devices 40 and/or the like. Each of the components of the system may be in electronic communication with, for example, one another over the same or different wireless or wired networks 30 including, for example, a wired or wireless Personal Area Network (PAN), Local Area Network (LAN), Metropolitan Area Network (MAN), Wide Area Network (WAN), and/or the like. Additionally, while FIG. 1 illustrates certain system devices as separate, standalone devices, the various embodiments are not limited to this particular architecture.

Exemplary Seizure Event Prediction Computing Entity

FIG. 2 provides a schematic of a seizure event prediction computing entity 10 according to some embodiments of the present disclosure. In general, the terms computing device, entity, device, system, and/or similar words used herein interchangeably may refer to, for example, one or more computers, computing devices, computing entities, desktop computers, mobile phones, tablets, phablets, notebooks, laptops, distributed systems, terminals, servers or server networks, blades, gateways, switches, processing devices, set-top boxes, relays, routers, network access points, base stations, the like, and/or any combination of devices adapted to perform the functions, operations, and/or processes described herein. Such functions, operations, and/or processes may include, for example, transmitting, receiving, operating on, processing, displaying, storing, determining, generating/creating, monitoring, evaluating, comparing, and/or similar terms used herein interchangeably. In some embodiments, these functions, operations, and/or processes can be performed on data, content, information, and/or similar terms used herein interchangeably.

As indicated, in some embodiments, the seizure event prediction computing entity 10 may also include one or more network and/or communications interfaces 220 for communicating with various computing entities, such as by communicating data, content, information, and/or similar terms used herein interchangeably that can be transmitted, received, operated on, processed, displayed, stored, and/or the like.

As shown in FIG. 2, In some embodiments, the seizure event prediction computing entity 10 may include or be in communication with one or more processing elements 205 (also referred to as processors, processing circuitry, and/or similar terms used herein interchangeably) that communicate with other elements within the seizure event prediction computing entity 10 via a bus, for example. As will be understood, the processing element 205 may be embodied in a number of different ways. For example, the processing element 205 may be embodied as one or more complex programmable logic devices (CPLDs), microprocessors, multi-core processors, coprocessing devices, application-specific instruction-set processors (ASIPs), and/or controllers. Further, the processing element 205 may be embodied as one or more other processing devices or circuitry. The term circuitry may refer to an entire hardware embodiment or a combination of hardware and computer program products. Thus, the processing element 205 may be embodied as integrated circuits, application specific integrated circuits (ASICs), field-programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present disclosure when configured accordingly.

In some embodiments, the seizure event prediction computing entity 10 may further include or be in communication with non-volatile media (also referred to as non-volatile storage, memory, memory storage, memory circuitry and/or similar terms used herein interchangeably). In some embodiments, the non-volatile storage or memory may include one or more non-volatile storage or memory media 210 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably may refer to a structured collection of records or information/data that is stored in a computer-readable storage medium, such as via a relational database, hierarchical database, and/or network database.

In some embodiments, the seizure event prediction computing entity 10 may further include or be in communication with volatile media (also referred to as volatile storage, memory, memory storage, memory circuitry and/or similar terms used herein interchangeably). In some embodiments, the volatile storage or memory may also include one or more volatile storage or memory media 215 as described above, such as RAM, DRAM, SRAM, FPM DRAM, EDO DRAM, SDRAM, DDR SDRAM, DDR2 SDRAM, DDR3 SDRAM, RDRAM, RIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 205. Thus, the databases, database instances, database management system entities, data, applications, programs, program modules, scripts, source code, object code, byte code, compiled code, interpreted code, machine code, executable instructions, and/or the like may be used to control certain aspects of the operation of the seizure event prediction computing entity 10 with the assistance of the processing element 205 and the operating system.

As indicated, in some embodiments, the seizure event prediction computing entity 10 may also include one or more network and/or communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, seizure event prediction computing entity 10 may be configured to communicate via wireless external communication networks using any of a variety of protocols, such as general packet radio service (GPRS), Universal Mobile Telecommunications System (UMTS), Code Division Multiple Access 200 (CDMA200), CDMA200 1x (1xRTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), IR protocols, NFC protocols, RFID protocols, IR protocols, ZigBee protocols, Z-Wave protocols, 6LoWPAN protocols, Wibree, Bluetooth protocols, wireless universal serial bus (USB) protocols, and/or any other wireless protocol. The seizure event prediction computing entity 10 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the seizure event prediction computing entity's components may be located remotely from other seizure event prediction computing entity 10 components, such as in a distributed system. Furthermore, one or more of the components may be aggregated and additional components performing functions described herein may be included in the seizure event prediction computing entity 10. Thus, the seizure event prediction computing entity 10 can be adapted to accommodate a variety of needs and circumstances, such as including various components described with regard to a mobile application executing on the user computing entity 20, including various input/output interfaces.

Exemplary User Computing Entity

The user computing entity 20 may be in communication with the seizure event prediction computing entity 10 and the wearable device 40. The user computing entity 20 may obtain and provide (e.g., transmit/send) data objects describing raw data (e.g., sensor data and/or physiological data associated with the user) obtained by one or more additional sensors or sensing devices, captured by another user computing entity 20 or device and/or provided by another computing entity. The user computing entity 20 may be configured to provide (e.g., transmit, send) data objects describing at least a portion of the sensor data and/or physiological data to the seizure event prediction computing entity 10. Additionally, in various embodiments, a remote computing entity may provide data objects describing user information/data to the seizure event prediction computing entity 10. In some embodiments, a user (e.g., wearer) of the wearable device 40 may operate the wearable device 40 via the display 316 or keypad 318 of the user computing entity 20.

FIG. 3 provides an illustrative schematic representative of user computing entity 20 that can be used in conjunction with embodiments of the present disclosure. In various embodiments, the user computing entity 20 may be or comprise one or more mobile devices in certain embodiments. For example, a user computing entity 20 may be embodied as a user's mobile device, carried by the user, and therefore the user computing entity 20 may be in close proximity to a wearable device worn by the user, such that close-range wireless communication technologies may be utilized for communicating between a controller of a wearable device and the user computing entity 20.

As shown in FIG. 3, a user computing entity 20 can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various devices, such as a seizure event prediction computing entity 10, another user computing entity 20, and/or the like. In an example embodiment, the transmitter 304 and/or receiver 306 are configured to communicate via one or more SRC protocols. For example, the transmitter 304 and/or receiver 306 may be configured to transmit and/or receive information/data, transmissions, and/or the like of at least one of Bluetooth protocols, low energy Bluetooth protocols, NFC protocols, RFID protocols, IR protocols, Wi-Fi protocols, ZigBee protocols, Z-Wave protocols, 6LoWPAN protocols, and/or other short range communication protocol. In various embodiments, the antenna 312, transmitter 304, and receiver 306 may be configured to communicate via one or more long range protocols, such as GPRS, UMTS, CDMA200, 1×RTT, WCDMA, GSM, EDGE, TD-SCDMA, LTE, E-UTRAN, EVDO, HSPA, HSDPA, Wi-Fi, Wi-Fi Direct, WiMAX, and/or the like. The user computing entity 20 may also include one or more network and/or communications interfaces 320 for communicating with various computing entities, such as by communicating data, content, information, and/or similar terms used herein interchangeably that can be transmitted, received, operated on, processed, displayed, stored, and/or the like.

In this regard, the user computing entity 20 may be capable of operating with one or more air interface standards, communication protocols, modulation types, and access types. More particularly, the user computing entity 20 may operate in accordance with any number of wireless communication standards and protocols. In a particular embodiment, the user computing entity 20 may operate in accordance with multiple wireless communication standards and protocols, such as GPRS, UMTS, CDMA200, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 20 can communicate with various other devices using concepts such as Unstructured Supplementary Service information/data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 20 can also download changes, add-ons, and updates, for instance, to its firmware, software (e.g., including executable instructions, applications, program modules), and operating system.

According to some embodiments, the user computing entity 20 may include location determining aspects, devices, modules, functionalities, and/or similar words used herein interchangeably to acquire location information/data regularly, continuously, or in response to certain triggers. For example, the user computing entity 20 may include outdoor positioning aspects, such as a location module adapted to acquire, for example, latitude, longitude, altitude, geocode, course, direction, heading, speed, UTC, date, and/or various other information/data. In some embodiments, the location module can acquire information/data, sometimes known as ephemeris information/data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data may be determined by triangulating the apparatus's 30 position in connection with a variety of other systems, including cellular towers, Wi-Fi access points, and/or the like. Similarly, the user computing entity 20 may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing entities (e.g., smartphones, laptops) and/or the like. For instance, such technologies may include iBeacons, Gimbal proximity beacons, BLE transmitters, NFC transmitters, and/or the like. These indoor positioning aspects can be used in a variety of settings to determine the location of someone or something to within inches or centimeters.

The user computing entity 20 may also comprise a user interface device comprising one or more user input/output interfaces (e.g., a display 316 and/or speaker/speaker driver coupled to a processing element 308 and a touch interface, keyboard, mouse, and/or microphone coupled to a processing element 308). For example, the user interface may be configured to provide a mobile application, browser, interactive user interface, dashboard, webpage, and/or similar words used herein interchangeably executing on and/or accessible via the user computing entity 20 to cause the display or audible presentation of information/data and for user interaction therewith via one or more user input interfaces. Moreover, the user interface can comprise or be in communication with any of a number of devices allowing the user computing entity 20 to receive information/data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 20 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 20 can capture, collect, store information/data, user interaction/input, and/or the like.

The user computing entity 20 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, information/data, applications, programs, program modules, scripts, source code, object code, byte code, compiled code, interpreted code, machine code, executable instructions, and/or the like to implement the functions of the user computing entity 20.

Exemplary Seizure Event Prediction System

FIG. 4 is a schematic diagram of an example system architecture 400 for generating seizure event predictions that can be used to perform one or more prediction-based tasks. The architecture 400 includes a seizure event prediction system 401 that is configured to receive data from the client computing entities 102, process the data to generate predictive outputs (e.g., seizure event prediction data objects), and provide the outputs to the client computing entities 102 for generating user interface data and/or dynamically updating a user interface. In some embodiments, seizure event prediction system 401 may communicate with at least one of the client computing entities 402 using one or more communication networks. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The seizure event prediction system 401 may include a seizure event prediction computing entity 406 and a storage subsystem 408. The seizure event prediction computing entity 406 may be configured to receive queries, requests and/or data from client computing entities 402, process the queries, requests and/or data to generate predictive outputs, and provide (e.g., transmit, send, and/or the like) the predictive outputs to the client computing entities 402. The client computing entities 402 may be configured to transmit requests to the seizure event prediction computing entity 406 in response to queries. Responsive to receiving the predictive outputs, the client computing entities 402 may generate user interface data and may provide (e.g., transmit, send and/or the like) user interface data for presentation by user computing entities.

The storage subsystem 408 may be configured to store at least a portion of the data utilized by the seizure event prediction computing entity 406 to perform seizure event prediction operations and tasks. The storage subsystem 408 may be configured to store at least a portion of operational data and/or operational configuration data including operational instructions and parameters utilized by the seizure event prediction computing entity 406 to perform seizure event prediction operations/tasks in response to requests. The storage subsystem 408 may include one or more storage units, such as multiple distributed storage units that are connected through a computer network. Each storage unit in the storage subsystem 408 may store at least one of one or more data assets and/or one or more data about the computed properties of one or more data assets. Moreover, each storage unit in the storage subsystem 408 may include one or more non-volatile storage or memory media including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Wearable Device

FIG. 5 is a schematic diagram illustrating an example wearable device 40 in accordance with some embodiments of the present disclosure. In various embodiments, the wearable device 40 is configured to (e.g., via one or more included sensors) detect a predefined seizure triggering condition in a user's field of view (also referred to herein as a wearer's field of view), and generate a seizure event prediction based at least in part on the at least one predefined seizure triggering condition, one or more predefined head movement features and/or one or more predefined facial movement features. Additionally, the wearable device 40 may cause initiation of a seizure response protocol in response to generating a seizure event prediction that satisfies certain parameters.

As noted above, the wearable device 40 may be or comprise an article configured to be worn proximate or adjacent a wearer's head and/or face. As depicted in FIG. 5, the wearable device 40 comprises eyewear (e.g., spectacles, glasses or the like) configured to be worn over or adjacent the wearer's eyes. As depicted in FIG. 5, the wearable device 40 comprises a frame having a plurality of elements attached thereto. As illustrated, at least a portion of the frame is configured to be secured over a wearer's ears. In various embodiments the frame may comprise plastic, fabric, metal, combinations thereof, and/or the like. In some embodiments, the wearable device 40 may be or comprise a hat, cap, face shield, visor, headphones, earphones, an earpiece, a watch, combinations thereof, and/or the like. In some embodiments, the wearable device 40 may comprise one or more sensors such as IMUs, image sensors, accelerometers, gyroscopes, combinations thereof, and/or the like. In some embodiments, as depicted in FIG. 5, the example wearable device 40 comprises at least a controller 502 (e.g., processor and/or a wireless communication transceiver), a power source 504 (e.g., a rechargeable battery), a first IMU 501, a second IMU 503, a third IMU 505, a first image sensor 507, a second image sensor 509, a first lens 511, and a second lens 513.

In some embodiments, the controller 502 of the wearable device 40 (e.g., which may comprise a computing device, one or more computer processors, or the like) may include a wireless communication transceiver and/or the like. In various embodiments, the controller 502 of the wearable device 40 may comprise components similar or identical to the user computing entity 20 depicted in FIG. 3. The controller 502 may be integrated into or attached to any surface of the wearable device 40 and may be in wired or wireless communication with sensors (e.g., the first IMU 501, the second IMU 503, the third IMU 505, the first image sensor 507 and the second image sensor 509) of the wearable device 40, and the power source 504 of the wearable device, the first lens 511 and/or the second lens 513 of the wearable device 40. Accordingly, the controller 502 of the wearable device 40 may be configured to (e.g., alone or together with the seizure event prediction computing entity 10) provide appropriate signals to elements of the wearable device 40 in order to initiate a seizure response protocol and thus prevent or mitigate a seizure event (e.g., cause an opacity change to at least a surface of the first lens 511 and/or the second lens 513). In some embodiments, the controller 502 may be in wireless communication with, but be physically distinct from, the wearable device 40 (e.g., via short-range wireless communication, such as Bluetooth communication, via long-range wireless communication, and/or the like), which may encompass a wireless receiver, thereby enabling appropriate signals to be passed to the wearable device 40 as discussed herein. In certain embodiments, the controller 502 may comprise an input/output interface system comprising one or more user input/output interfaces (e.g., a button, a display, and a touch interface, and/or a microphone coupled to a processing element and/or controller). For example, the user interface may be configured to cause display of or present audible presentation of information/data and for user interaction therewith via one or more user input interfaces. The controller may store instructions/parameters required for various operations by the wearable device 40.

In various embodiments, the wearable device 40 comprises at least one sensor (e.g., at least one of one or more IMUs, image sensors, accelerometers, gyroscopes, combinations thereof, and/or the like). The at least one sensor may be positioned at least partially on any interior or exterior surface of the wearable device 40 (e.g., on a frame). In certain embodiments, the at least one sensor enables receiving and/or capturing biometric inputs and/or information/data (e.g., regularly, continuously, and/or in response to certain triggers). For example, the at least one sensor may be configured to capture raw user sensor data. In some embodiments, the wearable device 40 may comprise microelectromechanical (MEMS) components, biological and chemical sensing components, electrocardiogram (ECG) components, electromyogram (EMG) components, electroencephalogram (EEG)-based neural sensing components, optical sensing components, electrical sensing components, sound components, vibration sensing components, accelerometer(s), pressure sensor(s) and/or the like. In certain embodiments, the at least one sensor may comprise a plurality of sensors of various sensor types to capture multiple data types. In certain embodiments, sensor data from one or more sensors (e.g., an IMU) may be analyzed (e.g., locally by the controller 502 of the wearable device 40 or via the seizure event prediction computing entity 10) to generate a seizure event prediction. Through such components, various types of physiological information/data can be captured—such as body position and/or movement data/information, heart rate information/data, oxygen saturation information/data, body temperature information/data, breath rate information/data, perspiration information/data, neural information/data, cardiovascular sounds information/data, and/or various other types of information/data. The one or more sensors of the wearable device 40 may be in electronic communication with the controller 502 of the wearable device 40 such that they can exchange information/data (e.g., receive and transmit data) with the wearable device 40. Additionally, sensor data may be collected and/or generated by one or more sensors associated with the user, such as mobile device sensors, other wearable device sensors (e.g., a smartwatch), sensors associated with one or more devices commonly used by the user (e.g., a glucose monitoring device), and/or the like.

As depicted in FIG. 5, the example wearable device 40 comprises a first image sensor 507 and a second image sensor 509. In various embodiments, each of the first image sensor 507 and the second image sensor 509 may be attached to a surface (e.g., inner surface or outer surface) of the wearable device 40 frame. Each of the first image sensor 507 and the second image sensor 509 may be or comprise a full spectrum camera, infrared camera, combinations thereof, and/or the like. At least one of the first image sensor 507 and the second image sensor 509 may be configured to monitor a wearer's field of view in order to detect a seizure triggering condition. The field of view may be a forward facing region that includes the wearer's line of sight. By way of example, the wearer's field of view may span 180 degrees from left to right (e.g., a semicircular area). The seizure triggering condition may be a visual feature (e.g., visual pattern, intensity of light, strobing light, changing color profiles, irregular geometric shape(s), and/or the like) or object within a person's field of view that can trigger a seizure. In some examples, identifying a seizure triggering condition comprises dividing each frame into clusters (e.g., a predefined number of pixels) and performing pixel analysis operations. In some embodiments, performing pixel analysis operations comprises performing photo luminance testing such as monitoring for an above-threshold change in luminance and identifying the seizure triggering condition in an instance in which an event (e.g., a flashing light, sudden or repeated movements) is repeated a certain number of times. In some examples, performing pixel analysis comprises performing contrast testing such as monitoring for visual contrast changes in pixel groups such as by detecting motion or pulsations. In some embodiments, identifying a seizure triggering condition may comprise performing both photo luminance testing and contrast testing techniques. In an instance in which a seizure triggering condition is identified, the controller 502 of the wearable device 40 may correlate a region of the first lens 511 and second lens 513 to a position of the seizure triggering condition in the user's field of view. In some embodiments, identifying the seizure triggering condition may also comprise assessing a plurality of additional parameters including a user's current activity (e.g., by analyzing speed of travel to determine whether the user is driving), determining a prediction time associated with the seizure triggering condition, and/or the like.

Additionally, at least one of the first image sensor 507 and the second image sensor 509 may be configured to capture image sensor data (e.g., images, video, combinations thereof, and/or the like) associated with the wearer's face. In some embodiments, subsequent identifying a seizure triggering condition, the wearable device 40 may be triggered to obtain sensor data (e.g., capture image data) associated with the wearer's face.

As further depicted in FIG. 5, the example wearable device 40 comprises a first IMU 501 attached to a left side of the wearable device 40 frame, a second IMU 503 attached to a central portion of the wearable device 40 frame, and a third IMU 505 attached to a right side of the wearable device 40 frame. It should be understood that each of the first IMU 501, the second IMU and the third IMU 505 may be attached to any interior or exterior surface of the wearable device 40 and in some examples may be integrated within the wearable device 40. Each of the first IMU 501, the second IMU and the third IMU 505 may detect and report measurements associated with a body's specific force, angular rate, orientation, acceleration, angular velocity, and/or the like. An example IMU may include one or more accelerometers, gyroscopes and magnetometers. In some embodiments, each of the first IMU 501, the second IMU and the third IMU 505 may be configured to detect and record measurements (e.g. three dimensional rotations and/or accelerations) relating to a wearer's head movements.

As further depicted in FIG. 5, the example wearable device 40 comprises a first lens 511 and a second lens 513 configured to be worn adjacent the wearers eyes. In some embodiments, each of the first lens 511 and the second lens 513 of the wearable device 40 may be or comprise at least one transparent surface that is capable of exhibiting opacity changes in response receiving a control indication. In some embodiments, the at least one transparent surface may comprise a glass material comprising a PLDC film or laminate, or other similar material.

Referring now to FIG. 6, an operational example 600 depicting opacity changes in accordance with some embodiments of the present disclosure is provided. As illustrated, in a first view 601, the lenses of an example wearable device appear transparent when in an inactive or baseline state. As further depicted in FIG. 6, in a second view 603, in response to receiving a control indication (e.g., an electric current supplied by the controller 502, power source 504 and/or other electrical device) at least a portion of each of the lenses of the example wearable device exhibits opacity changes and appears darker/opaque in contrast with the first view 601. For example, a portion of a first lens and/or a portion of a second lens may be configured to exhibit opacity changes. In some embodiments, particular portions/regions of one or both of the lenses may be activated as a seizure triggering condition (e.g., an object) moves from one location to another within the user's field of view. In some embodiments, as depicted in the second view 603, the activated portions of the lenses are aligned with a location of a seizure triggering condition (e.g., object, light, and/or the like) in the user's field of view. In some embodiments, for example, in response to detecting that a seizure triggering condition has ceased, the wearable device may provide a second control indication to reverse the opacity changes (e.g., revert to the baseline state depicted in first view 601). In some examples, opacity changes may be triggered based at least in part on the user's current activity. For example, opacity changes may be triggered if a user is outside or driving, but not if a user is inside a building and/or sitting down.

Returning to FIG. 5, in certain embodiments, the controller 502 of the wearable device 40 may be configured to locally execute various algorithms on at least a portion of the raw and/or processed information/data obtained by the wearable device 40. For example, the controller 502 of the wearable device 40 may be configured to generate a seizure event prediction with respect to a wearer (e.g., in conjunction with one or more onboard sensors). In other embodiments, the controller 502 of the wearable device 40 transmits data objects describing at least a portion of the raw and/or processed information/data for processing by the seizure event prediction computing entity 10. As part of processing the raw data received from the one or more sensors, the controller 502 of the wearable device 40 may be configured to receive data objects describing additional information (e.g., physiological data, biological data, and the like) from a user computing entity 20 and/or from the seizure event prediction computing entity 10. Such additional information may be utilized for determining appropriate control signals in conjunction with a seizure response protocol in order to prevent or mitigate a seizure event. In some embodiments, the controller 502 of the wearable device 40 may be configured to transmit (periodically or on request) data objects describing at least a portion of the raw data to the seizure event prediction computing entity 10 for processing. The controller 502 of the wearable device 40 may be configured to obtain (e.g., request and receive), a user profile data object (e.g., comprising seizure response protocols for a plurality of different user states) from the seizure event prediction computing entity 10 and store the user profile data object. The controller 502 of the wearable device 40 may cause initiation of a seizure response protocol based at least in part on a determination that the user's current state satisfies particular criteria associated with a seizure response protocol. By way of example, based at least in part on at least one predefined seizure triggering condition, the wearable device 40 may provide a control indication to cause opacity changes to at least one surface (e.g., one or more lenses) of the wearable device 40. In some embodiments, the wearable device 40 comprises a power source 504 (e.g., one or more batteries) to provide power to the onboard controller 502 (e.g., and, in some examples, a current generator or circuit operatively coupled to the lenses of the wearable device 40).

In various embodiments, each of the elements of the wearable device 40 (e.g., the first IMU 501, the second IMU 503, the third IMU 505, the first image sensor 507, the second image sensor 509, the first lens 511 and the second lens 513) is in electronic communication with the wearable device 40 such that it can exchange information/data (e.g., receive and transmit data, data objects and the like) with the wearable device 40 controller/processor.

As discussed herein, the controller 502 may comprise one or more control elements for transmitting a control signal to control (e.g., adjust or modify) various operations and operational parameters of the wearable device 40. For example, the user may control (e.g., override) the wearable device 40, for example in order to adjust features of or stop operations of the wearable device 40. In another example, a user may transmit a control signal to adjust opacity change features (e.g., increase opacity, reduce opacity, or the like).

Moreover, the controller 502 may additionally comprise an emergency assistance call system (e.g., comprising a user interface element, such as a button, a transmitter for sending an emergency assistance signal to an external system, and/or the like) that is configured to call for emergency assistance (e.g., an ambulance) upon the occurrence of certain trigger events. For example, the emergency assistance call system may be configured to call for emergency assistance upon the user interacting with the included user interface element. In other embodiments, the emergency assistance call system may be integrated with the various sensors discussed above, and may be configured to automatically call for emergency assistance upon the controller 502 sensing the user is experiencing a seizure.

V. Exemplary Steps/Operations

As described below, the apparatuses, systems, and methods described herein provide a robust seizure event detection and prevention system. Moreover, various embodiments of the present invention disclose seizure prediction machine learning models that can make inferences based on sensory data in order to perform seizure event/seizure event type detection in a more computationally manner compared to the state-of-the-art systems. Accordingly, various embodiments of the present disclosure make substantial technical contributions to the field of monitoring devices and substantially improve state-of-the-art systems.

FIG. 7, FIG. 8 and FIG. 9 are flowcharts illustrating example steps, processes, procedures, and/or operations for generating a seizure event prediction; FIG. 10 provides an operational example of generating a seizure event prediction. Although the following exemplary operations are described as being performed by one of the wearable device 40 (e.g., via the controller 502), the seizure event prediction computing entity 10, or the user computing entity 20, it should be understood that in various embodiments, the operations can be interchangeably performed by other components within the system architecture 100.

Various embodiments may be configured to utilize one or more user profiles (e.g., a user-specific user seizure profile) to facilitate operations of the wearable device 40. The user-specific user seizure profile may comprise data indicative of features of the user (e.g., data indicative of the user's age, gender, medical conditions, and/or the like, which may be obtained from electronic medical record (EMR) data stored in a data storage area and associated with the user), as well as data indicative of functional results of operations of the wearable device (e.g., data relating to historical seizure events) determined based at least in part on the operation of the sensors of the wearable device 40. Accordingly, the seizure event prediction computing entity 10 may be configured to obtain (e.g., receive) and process data objects describing raw data (sensor data, physiological data, user profile information/data and/or the like) associated with a user in order to generate a user seizure profile for the user. An example user seizure profile may define a set of threshold values and/or features (e.g., head movement features and facial movement features) associated with a particular seizure event type (e.g., aura stage, ictal stage). Accordingly, each seizure event type may be associated with a seizure event feature set. The user seizure profile may be stored in conjunction with or otherwise associated with a user profile data object. The seizure event prediction computing entity 10 may be configured to generate or identify, based at least in part on the user seizure profile and user profile information, a plurality of seizure event protocols each corresponding with at least one seizure event feature set for the user.

By way of example, a seizure event protocol for an aura stage of seizure may recommend providing an audio alert to a user. In another example, a seizure event protocol for an ictal stage of seizure may recommend generating and sending a report to a clinician. The seizure response protocol(s) and user seizure profile may be stored in conjunction with or otherwise associated with the user profile data object. In some embodiments, an operator (e.g., a clinician) interfacing with the seizure event prediction computing entity 10 may modify the user seizure profile and/or seizure response protocols associated with the user profile data object. The seizure event prediction computing entity 10 may be configured to store and/or in turn provide (e.g., send, transmit) a user profile data object comprising the user seizure profile and the stored seizure response protocols to the wearable device 40. The seizure event prediction computing entity 10 may be configured to obtain (e.g., receive, request) and process a data object describing raw data (e.g., sensor data) collected by sensors of the wearable device 40 and/or other sensors and sensing devices associated with the user in order to update the user seizure profile and the stored seizure response protocols for the user. The seizure event prediction computing entity 10 may be configured to process (periodically or in response to receiving particular data) additional data/information associated with the user in order to update (e.g., adjust, change) the user seizure profile and/or stored seizure response protocols for the user. The seizure event prediction computing entity 10 may periodically provide (e.g., send, transmit) an updated user profile data object comprising the most up-to-date user seizure profile and seizure response protocols to the wearable device 40. The seizure event prediction computing entity 10 may generate a user interface data object corresponding with the user profile data object and provide (e.g., transmit, send, and/or the like) the user interface data object to one or more a user computing entities 20 or other computing entities (e.g., other computing entities operated by the user, clinicians and/or the like) for presentation by the noted computing entities.

Seizure Detection and Prevention

In various embodiments, an example wearable device 40 may be configured to generate a seizure event prediction (e.g., identify a seizure event). In various embodiments, a wearable device 40 may be configured to store a user seizure profile defining a plurality of seizure event feature sets that are each associated with a seizure event type. The seizure event feature sets may be utilized to determine whether the wearer is experiencing or likely to experience a seizure event. Accordingly, a corresponding seizure response protocol may be identified and initiated.

The user seizure profile may differ between individual users. For example, pupils of a first user may dilate when the first user is an aura stage of a seizure but pupils of a second user may not dilate when the user is in an aura stage. Accordingly, the seizure event feature sets may differ based at least in part on unique features and responses of each individual user. The wearable device 40 may be configured to generate a seizure event prediction based at least in part on sensor data collected in real-time from one or more sensors of the wearable device. In an instance in which one or more features satisfy a seizure event feature set threshold, the wearable device 40 may identify and initiate a corresponding seizure response protocol. An example seizure response protocol may comprise causing opacity changes to at least one surface of the wearable device 40, generating an alert, transmitting an indication to another computing entity, storing at least a portion or relevant sensor data, and/or generating an event report. Determining whether a seizure event feature set threshold is satisfied for a particular user may be based at least in part on features of the user, features of the user's current activity, data indicative of the user's current location, and/or the like.

Referring now to FIG. 7, a flowchart diagram illustrating an example process 700 for generating a seizure event prediction by a seizure event prediction computing entity 10 (or wearable device 40) in accordance with some embodiments of the present disclosure is provided.

Beginning at step/operation 702, seizure event prediction computing entity 10 identifies a seizure triggering condition. As noted above, the seizure triggering condition may comprise visual features (e.g., an object, a visual pattern, light intensity, frequency of strobing light and/or the like) within a person's field of view that can trigger a seizure. In some embodiments, in response to identifying the seizure triggering condition, the seizure event prediction computing entity 10 may trigger one or more sensors of a wearable device to obtain sensor data associated with a user's face movements and head movements.

Subsequent to step/operation 702, the process 700 proceeds to step/operation 704. At step/operation 704, seizure event prediction computing entity 10 identifies, using a seizure event prediction machine learning model, one or more predefined head movement features and one or more predefined facial movement features. The seizure event prediction machine learning model may be a data object that describes steps/operations, hyper-parameters, and/or parameters of a machine learning model/algorithm that is configured to generate a seizure event prediction with respect to a wearer of a wearable device. The steps/operations of the seizure event prediction machine learning model may enable performing one or more prediction-based tasks (e.g., triggering a seizure response protocol). In some embodiments, the seizure event prediction machine learning model may comprise a first sub-model that is configured to identify the seizure triggering condition in a user's field of view. In some embodiments, the seizure event prediction machine learning model may comprise a second sub-model that is configured to identify one or more predefined head movement features and one or more predefined facial movement features associated with a user's head movements and facial movements. In some embodiments, the predefined head movement features may comprise three dimensional head rotations and/or accelerations. In some embodiments, the predefined facial movement features may comprise eye movements (e.g., a fixed gaze for a predefined length of time), a tasting gesture, and a pupil size change. The second sub-model of the seizure event prediction machine learning model may identify the one or more head movement features and the one or more facial movement features using a Eulerian video processing technique. The seizure event prediction machine learning model may be trained based at least in part on a ground truth seizure event. In some embodiments, the seizure event prediction machine learning model may be trained based at least in part on user-specific data such as sensor data depicting the user making a tasting gesture or experiencing seizure(s). By way of example, the seizure event prediction machine learning model/algorithm may be a neural network, a convolutional neural network (CNN), a recurrent neural network (RNN), and/or the like.

Subsequent to step/operation 704, the process 700 proceeds to step/operation 706. At step/operation 704, seizure event prediction computing entity 10 generates a seizure event prediction based at least in part on the seizure triggering condition, the one or more head movement features, and the one or more facial movement features. The seizure event prediction may be a data object that describes a predictive output of one or more computer-implemented processes, wherein the predictive output describes an inferred determination relating to whether or not a person is experiencing or is likely to experience a seizure within a predefined period of time (e.g., one hour, six hours or the like). In some embodiments, determining a seizure event prediction may comprise processing an event data object describing sensor data associated with a user of a wearable device. In some embodiments, the seizure event prediction may be a value (e.g., a percentage value, number between 0 and 1, or value within a certain range), where an above-threshold value indicates that a person (e.g., a user of a wearable device) is experiencing or likely to experience a particular type of seizure event within a predefined time period.

By generating seizure event predictions, the apparatuses, systems, and methods described herein provide a robust seizure event detection and prevention system. Moreover, various embodiments of the present invention disclose seizure prediction machine learning models that can make inferences based on sensory data in order to perform seizure event/seizure event type detection in a more computationally manner compared to the state-of-the-art systems. Accordingly, various embodiments of the present disclosure make substantial technical contributions to the field of monitoring devices and substantially improve state-of-the-art systems.

In some embodiments, step/operation 706 may be performed in accordance with the process 800 of FIG. 8, which is a flowchart diagram illustrating an example process 800 for generating a seizure event prediction by a wearable device 40 in accordance with some embodiments of the present disclosure is provided.

Beginning at step/operation 802, the controller 502 of the wearable device 40 may be configured to generate an event data object for a wearer of the wearable device 40. The event data object may be a data object storing and/or providing access to information/data with respect to a user of a wearable device. In some embodiments, an event data object may describe one or more recorded events that have been recorded to have occurred in relation to a user of a wearable device. In some embodiments, the event data object may comprise sensor data (e.g., image data, acceleration data, and/or the like) associated with one or more of the user's face, the user's head movements, and the user's field of view.

Subsequent to generating the event data object at step/operation 802, at step/operation 804, the controller 502 of the wearable device 40 provides the event data object to the seizure event prediction computing entity 10. In some embodiments, the controller 502 of the wearable device 40 may obtain (e.g., collect) user sensor data via one or more sensors (e.g., IMUs, image sensors, and/or the like) of a wearable device 40 for an initial time period and generate and transmit a user sensor data object describing at least a portion of the obtained user sensor data to the seizure event prediction computing entity 10.

At step/operation 806, the controller 502 of the wearable device obtains (e.g., requests, receives, or the like) a user profile data object comprising a user seizure profile and corresponding seizure response protocols from the seizure event prediction computing entity 10. The controller 502 of the wearable device 40 may, in certain embodiments, receive an applicable stored user profile for a user based at least in part on user input received via a user interface of the wearable device 40 (or based at least in part on user input data received from a user computing entity associated with the wearable device 40). It should be understood that an appropriate user profile data object may be identified via any of a variety of alternative mechanisms, such as by identifying a user profile associated with a particular user computing entity (e.g., the user profile of a designated owner of a user computing entity) that is within communication range of the wearable device 40. In some embodiments, the wearable device 40 may request the user profile data object from the seizure event prediction computing entity 10. The controller 502 of the wearable device 40 may periodically request an updated user profile data object for the wearer of the wearable device 40 from the seizure event prediction computing entity 10. In some embodiments, the controller 502 of the wearable device 40 may generate at least a portion of data stored within the user profile data object. In one example, the controller of the wearable device 40 may generate an initial user profile data object for a user based at least in part on evaluation of user sensor data collected via one or more sensors of the wearable device 40 while the user is wearing the wearable device 40. In some embodiments, the wearable device 40 may determine initial operating parameters and/or generate a user seizure profile by monitoring the user (e.g., obtaining and analyzing sensor data collected via one or more sensors of the wearable device 40 for an initial time period). In some embodiments, the wearable device 40 may provide (e.g., transmit, send) an event data object to the seizure event prediction computing entity 10 for generating and storing the user seizure profile within a data storage area associated with the seizure event prediction computing entity 10. Subsequent to periodically receiving new information and/or data, the wearable device 40 or seizure event prediction computing entity 10 may update the user seizure profile stored in conjunction with a user profile data object and provide (e.g., transmit) an updated user profile data object periodically and/or on request.

Subsequent to obtaining a user profile data object at step/operation 806, at step/operation 808, based at least in part on the monitored sensor data, the controller 502 of the wearable device 40 generates a seizure event prediction based on the event data object and the user profile data. Generating a seizure event prediction may comprise identifying a threshold number of features from a seizure event feature set associated with a seizure event type. For example, the controller 502 of the wearable device 40 may monitor the wearer's field of view and/or collects image data associated with the wearer's face and/or head. Additionally, the controller 502 of the wearable device 40 analyzes at least a portion of sensor data collected by one or more sensors of the wearable device 40 in order to identify one or more head movement features and/or facial movement features. The wearable device 40 may store at least a portion of the sensor data and/or results of the analysis in conjunction with the user profile data object. The wearable device 40 may store the sensor data in association with sensor identifier information/data (e.g., metadata, timestamp data and/or the like).

Returning to FIG. 7, at step/operation 708, the controller 502 of the wearable device 40, performs one or more prediction-based tasks based on the seizure event prediction. In some embodiments, in an instance in which the seizure event prediction satisfies certain parameters, the controller 502 identifies a seizure response protocol associated with the predicted seizure event. By way of example, the controller 502 of the wearable device 40 may determine that there is an above-threshold likelihood that the user is currently in an aura stage of seizure (e.g., is experiencing a pre-seizure event). Additionally, the controller 502 of the wearable device 40 may determine that a seizure response protocol associated with an aura stage of seizure for the user recommends providing an alert to the user and/or causing opacity changes to lenses of the wearable device 40. In another example, the controller 502 of the wearable device 40 may determine that there is an above-threshold likelihood that the user is currently in a prodrome phase of seizure. Additionally, the controller 502 of the wearable device 40 may determine that a seizure response protocol associated with the prodrome stage of seizure for the user recommends obtaining user biometric data from other wearable devices (e.g., a smartwatch, mobile device) and performing further analysis. In yet another example, the controller 502 of the wearable device 40 may determine that there is an above-threshold likelihood that the user is currently in an ictal stage of seizure. Additionally, the controller 502 of the wearable device 40 may determine that a seizure response protocol associated with the ictal stage of seizure for the user recommends providing an audio alert to individuals in a vicinity of the user in order to solicit assistance and/or activating emergency assistance call system.

Subsequent to causing initiation of the seizure response protocol, the controller 502 of the wearable device 40 may update the stored user profile data object based at least in part on data describing the predicted seizure event, the sensor data and/or the seizure event protocol. By updating the stored user profile data object, the stored user profile data object may be maintained to reflect a current state of data, e.g., by reflecting a user's response to early interventions. Subsequent seizure response protocols may be adjusted to reflect current features of the user, as reflected in the updated user profile data object.

Subsequent to updating the stored user profile data object, the controller 502 of the wearable device 40 may provide (e.g., transmit, send, and/or the like) the updated user profile data object to seizure event prediction computing entity 10. However, it should be understood that in certain embodiments, updating the stored user profile data object may comprise the controller 502 of the wearable device 40 providing updated data to the seizure event prediction computing entity 10, and the seizure event prediction computing entity 10 may update the stored user profile data object.

In some embodiments, step/operation 708 can be performed in accordance with FIG. 9, which is a flowchart diagram illustrating an example process 900 for providing an updated user profile data object to another computing entity, in accordance with some embodiments of the present disclosure is provided.

Beginning at step/operation 902, the seizure event prediction computing entity 10 obtains (e.g., receives) the event data object (e.g., from the wearable device 40).

Subsequent to obtaining the event data object at step/operation 902, at step/operation 904, the seizure event prediction computing entity obtains a user profile data object describing user information/data. In some embodiments, the user profile data object may be provided by a remote computing entity (e.g., a remote computing entity storing user EMR data). The user profile data object may describe various types of information associated with a particular user including, but not limited to, age, gender, weight, height, body mass index (BMI), weight distribution and/or the like. In some embodiments, user profile data objects describing user information may be provided by one or more computing entities, one or more other wearable or health management devices (e.g., fitness trackers), a mobile device and/or the like. In some embodiments, step/operation 904 may be performed as part of registering a user. For example, a user profile data object for a user may be generated/created as part of registration. However, as will be recognized, a user profile may already exist and be stored in a user profile database. In such a case, registration may link the user to an existing user profile. Each user profile may be identifiable via one or more identifiers (e.g., social security numbers, patient IDs, member IDs, participant IDs, usernames, one or more globally unique identifiers (GUIDs), universally unique identifiers (UUIDs), and/or the like) that are configured to uniquely identify the user profile. As part of registering a user, seizure event prediction computing entity 10 may obtain (e.g., request and receive) various data objects describing information/data associated with a user. In various embodiments, seizure event prediction computing entity 10 receives one or more data objects describing the user information/data for generation/creation of and/or storage in conjunction with a user profile data object. In some embodiments, a user's EMR may be associated with and/or otherwise stored in conjunction with the user profile data object. The seizure event prediction computing entity 10 may store the event data object in conjunction with the user profile data object.

Subsequent to obtaining the user profile data object at step/operation 904, at step/operation 906, based at least in part on the user information stored in a user profile data object and the event data object associated therewith, the seizure event prediction computing entity 10 generates a seizure event profile data object for the user. In some embodiments, a seizure event profile data object may define a plurality seizure event feature sets in which each seizure event feature set is associated with a particular set of features (e.g., head movement features and/or facial movement features). Accordingly, a seizure event feature set may comprise a defined set of features that are indicative of a particular type of seizure event. The seizure event feature set may be a set of values/amounts such as a head acceleration values and head rotation values. The seizure event feature set may be influenced by and determined based at least in part on additional user parameters (e.g., age, gender, body weight, height, historical seizure event data, and/or the like). Accordingly, the seizure event prediction computing entity 10 may be configured to periodically update the user seizure profile data as additional data for the user (e.g., changes in the user profile data object) is obtained so as to maintain an updated seizure event profile data object for the user. In some embodiments, the wearable device 40 may be configured to determine the user seizure profile for a user and provide (e.g., transmit, send) a user seizure profile data object to the seizure event prediction computing entity 10.

Subsequent to generating a seizure event profile data object at step/operation 906, at step/operation 908, the seizure event prediction computing entity 10 determines a plurality of seizure response protocols each corresponding with a seizure event feature set.

Then at step/operation 910, the seizure event prediction computing entity 10 stores the user seizure profile and corresponding seizure response protocols in association with the user profile data object. As noted, the user seizure profile for a user may be periodically updated (e.g., as new data is provided to a user's EMR, as the wearable device 40 is utilized over time, and/or the like). Accordingly, the controller 502 may implement a feedback loop that updates the seizure event profile data object for a user based at least in part on a determined accuracy relating to predicted seizure events and/or effectiveness of seizure response protocols. For example, the controller 502 (e.g., in conjunction with the seizure event prediction computing entity 10) may determine whether a particular opacity level was effective in preventing a seizure event. For example, the controller 502 may determine whether a duration of an opacity change should be increased or decreased based at least in part on whether the user experienced a seizure event within a predefined time period subsequent to being exposed to a seizure triggering condition.

Subsequent to storing the user seizure profile and corresponding seizure response protocols at step/operation 910, at step/operation 912, the seizure event prediction computing entity 10 provides (e.g., transmits, sends and/or the like) the user profile data object to the controller 502 of the wearable device 40 to facilitate operations.

At step/operation 914, seizure event prediction computing entity 10 periodically obtains an updated user profile data object describing user information and/sensor data obtained by controller 502 of the wearable device 40 including, e.g., intervention data, user response data, biometric data, and/or the like.

Subsequent to step/operation 914, at step/operation 916, in response to receiving an updated user profile data object, the seizure event prediction computing entity 10 updates the user seizure profile and/or seizure response protocols for the user which are stored in conjunction with user profile data object. The seizure event prediction computing entity 10 may update the user seizure profile and/or seizure response protocols based at least in part on new user EMR data, biometric data and/or sensor data provided by other computing entities and/or the like. In so doing, the seizure event prediction computing entity 10 can refine the outputs generated by the wearable device 40 over time and more accurately detect and prevent seizure events. Additionally, the most effective seizure response protocols for a particular user, and for particular types of seizure events across population subgroups can be identified over time. In certain embodiments, the seizure event prediction computing entity 10 may be configured to refine one or more seizure response protocols for a user using a seizure event machine learning model (e.g., a trained neural network). Moreover, updated information based at least in part on new user features (e.g., weight loss or weight gain, medical history including recent medical procedures and/or the like) can be provided for updating the user seizure profile and/or seizure event profile data object, which may be utilized to refine seizure response protocols to be utilized for certain population subgroups. In some embodiments, the user computing entity 20 and/or one or more other computing devices may be are configured to obtain (e.g., monitor, detect, and/or the like) additional body data and provide data object(s) associated therewith. The body data may be or comprise physiological information/data, biometric information/data, heart rate data, oxygen saturation data, pulse rate data, body temperature data, breath rate data, perspiration data, blood pressure data, neural activity data, cardiovascular data, pulmonary data, and/or various other types of information/data which may be relevant for updating the user profile data object storing the user seizure profile and/or corresponding seizure response protocols.

Subsequent to updating the user profile data object at step/operation 916, at step/operation 918, the seizure event prediction computing entity 10 transmits an updated user profile data object to the wearable device 40. In various embodiments, the seizure event prediction computing entity 10 and the wearable device 40 periodically update and provide (e.g., send, transmit) user profile data objects and in so doing effectively incorporate real-time user information and user profile information/data in continuous feedback loop.

Generating User Interface Data

In various embodiments, a variety of sources (e.g., seizure event prediction computing entity 10) may provide (e.g., transmit, send) a mobile application for download and execution on a user computing entity 20 (e.g., in response to a request to download the mobile application generated at the user computing entity 20). In another embodiment, the mobile application may be pre-installed on the user computing entity 20. And in yet another embodiment, the mobile application may be a browser executing on the user computing entity 20. The mobile application may comprise computer-executable program code (e.g., a software application) that provides the functionality described herein. The mobile application may enable various functionalities as discussed herein. Moreover, although specifically referenced as a mobile application, it should be understood that the mobile application may be executable by any of a variety of computing entity types, such as desktop computers, laptop computers, mobile devices, and/or the like. In various embodiments, instructions may be automatically generated (e.g., by the seizure event prediction computing entity 10) or provided based at least in part in response to clinician input/instructions provided by a clinician interacting with the seizure event prediction computing entity 10. The instructions may comprise messages in the form of banners, headers, notifications, and/or the like.

In some embodiments, at least a portion of the obtained wearable device sensor data may be transferred to the user computing entity 20 and/or the seizure event prediction computing entity 10 for performing at least a portion of the required operations. The wearable device 40 or user computing entity 20 may be configured to provide information/data in response to requests/queries received from the seizure event prediction computing entity 10. In various embodiments, the wearable device 40 may be managed, calibrated and/or otherwise controlled at least in part by a seizure event prediction computing entity 10. The seizure event prediction computing entity 10 may generate a user interface data object based at least in part on a user profile data object and provide (e.g., transmit, send) the user interface data object to one or more client computing entities.

FIG. 10 provides an operational example of a user interface data object generated by the seizure event prediction computing entity 10. The seizure event prediction computing entity 10 may generate an alert or notification based at least in part on data/information stored in association with a user profile data object. The wearable device 40/seizure event prediction computing entity 10 may provide one or more data objects corresponding with the alert/notification for presentation by a user computing entity 20 (e.g., for dynamically updating a user interface 1002 of a user computing entity 20). In one example, as depicted, the user interface 1002 of the user computing entity 20 provides an alert indicating that a wearer is 80% likely to be in the early stages of a seizure. Additionally, as depicted, the user interface 1002 may provide recommended actions for the user to take. As will be recognized, a variety of other approaches and techniques can be used to adapt to various needs and circumstances.

Accordingly, as described above, the apparatuses, systems, and methods described herein provide a robust seizure event detection and prevention system. Moreover, various embodiments of the present invention disclose seizure prediction machine learning models that can make inferences based on sensory data in order to perform seizure event/seizure event type detection in a more computationally manner compared to the state-of-the-art systems. Accordingly, various embodiments of the present disclosure make substantial technical contributions to the field of monitoring devices and substantially improve state-of-the-art systems.

VI. Conclusion

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only, and not for purposes of limitation.

The invention claimed is:

1. A computer-implemented method comprising:
receiving, by one or more processors and using a wearable device, an event data object comprising image sensor data indicative of (i) a movement of a face of a user and (ii) a field of view of the user;
inputting, by the one or more processors and to a seizure prediction machine learning model, the event data object;
obtaining, by the one or more processors and from the seizure prediction machine learning model, a seizure event prediction data object, wherein the seizure prediction machine learning model is configured to:
generate one or more predefined facial movement features based at least in part on the image sensor data indicative of the movement of the face of the user from the event data object;
generate a seizure event type that is determined based at least in part on the one or more predefined facial movement features;
generate a predefined seizure triggering condition based at least in part on the image sensor data indicative of the field of view of the user from the event data object; and generate the seizure event prediction data object based at least in part on the seizure event type and the predefined seizure triggering condition; and modifying, by the one or more processors and using the wearable device, an opacity of a transparent surface of the wearable device based at least in part on the seizure event prediction data object.

2. The computer-implemented method of claim 1, wherein the event data object further comprises sensor data indicative of a movement of a head of the user, and the computer-implemented method further comprises:
identifying one or more predefined head movement features from the event data object, wherein:
(i) the seizure event prediction data object is determined based at least in part on the one or more predefined head movement features,
(ii) the seizure prediction machine learning model comprises a first sub-model that is configured to identify the predefined seizure triggering condition in the field of view of the user, and a second sub-model that is configured to determine the one or more predefined head movement features and the one or more predefined facial movement features, and
(iii) the seizure event prediction data object is determined based at least in part on the predefined seizure triggering condition, the one or more predefined head movement features, the one or more predefined facial movement features, and the seizure event type.

3. The computer-implemented method of claim 2, wherein the second sub-model is configured to determine the one or more predefined head movement features and the one or more predefined facial movement features based at least in part on a Eulerian video processing technique.

4. The computer-implemented method of claim 1, further comprising:
providing, by the one or more processors, an indication of the seizure event prediction data object to a user computing entity; and
storing, by the one or more processors, information associated with the seizure event prediction data object to a user profile.

5. The computer-implemented method of claim 2, wherein the sensor data is captured in real-time by an inertial measurement unit (IMU) of the wearable device.

6. The computer-implemented method of claim 5, wherein the wearable device comprises:
an image sensor,
the IMU, and
a controller configured to:
monitor, via the image sensor, the field of view of the user;
detect the predefined seizure triggering condition in the field of view of the user;
responsive to identifying the predefined seizure triggering condition, generate a seizure event prediction; and
in an instance in which the seizure event prediction satisfies a seizure event prediction threshold, cause initiation of a seizure response protocol associated with the seizure event prediction.

7. The computer-implemented method of claim 1, wherein modifying the opacity of the transparent surface of the wearable device comprises:
modifying the opacity of at least one portion of a first and/or a second transparent surface of the wearable device.

8. The computer-implemented method of claim 1, further comprising:

responsive to detecting that at least one predefined seizure triggering condition has ceased, remodifying the opacity of the transparent surface of the wearable device.

9. The computer-implemented method of claim 1, wherein the one or more predefined facial movement features comprise at least one of rhythmic eye movements, a tasting gesture, or a pupil size.

10. The computer-implemented method of claim 2, wherein the one or more predefined head movement features comprise three-dimensional head rotations and accelerations.

11. The computer-implemented method of claim 1, wherein the transparent surface of the wearable device comprises a polymer dispersed liquid crystal (PDLC) film.

12. The computer-implemented method of claim 6, wherein the seizure response protocol comprises at least one of: (i) providing an audio alert, (ii) transmitting a notification to a computing entity in electronic communication with the wearable device, (iii) obtaining additional sensor data, or (iv) generating a report of the seizure event prediction data object.

13. The computer-implemented method of claim 6, wherein the controller of the wearable device is further configured to:
store at least a portion of the sensor data associated with the seizure event prediction data object; and
transmit the at least a portion of sensor data to a computing entity that is in electronic communication with the wearable device.

14. The computer-implemented method of claim 1, wherein the seizure prediction machine learning model comprises a trained neural network machine learning model.

15. A system comprising memory and one or more processors communicatively coupled with the memory, the one or more processors configured to:
receive, using a wearable device, an event data object comprising image sensor data indicative of (i) a movement of a face of a user and (ii) a field of view of the user;
input, to a seizure prediction machine learning model, the event data object;
obtain, from the seizure prediction machine learning model, a seizure event prediction data object, wherein the seizure prediction machine learning model is configured to:
generate one or more predefined facial movement features based at least in part on the image sensor data indicative of the movement of the face of the user from the event data object;
generate a seizure event type that is determined based at least in part on the one or more predefined facial movement features;
generate a predefined seizure triggering condition based at least in part on the image sensor data indicative of the field of view of the user from the event data object; and
generate the seizure event prediction data object based at least in part on the seizure event type and the predefined seizure triggering condition; and
modify, using the wearable device, an opacity of a transparent surface of the wearable device based at least in part on the seizure event prediction data object.

16. The system of claim 15, wherein the event data object further comprises sensor data indicative of a movement of a head of a user, and the one or more processors are further caused to:
identify one or more predefined head movement features from the event data object, wherein:

(i) the seizure event prediction data object is determined based at least in part on the one or more predefined head movement features, (ii) the seizure prediction machine learning model comprises a first sub-model that is configured to identify the predefined seizure triggering condition in the field of view of the user, and a second sub-model that is configured to determine the one or more predefined head movement features and the one or more predefined facial movement features, and (iii) the seizure event prediction data object is determined based at least in part on the predefined seizure triggering condition, the one or more predefined head movement features, the one or more predefined facial movement features, and the seizure event type.

17. One or more non-transitory computer-readable storage media comprising instructions that, when executed by one or more processors, cause the one or more processors to:

receive, from a wearable device, an event data object comprising image sensor data indicative of (i) a movement of a face of a user and (ii) a field of view of the user;

input, to a seizure prediction machine learning model, the event data object;

obtain, from the seizure prediction machine learning model, a seizure event prediction data object, wherein the seizure prediction machine learning model is configured to:

generate one or more predefined facial movement features based at least in part on the image sensor data indicative of the movement of the face of the user from the event data object;

generate, a seizure event type that is determined based at least in part on the one or more predefined facial movement features;

generate a predefined seizure triggering condition based at least in part on the image sensor data indicative of the field of view of the user from the event data object; and generate the seizure event prediction data object based at least in part on the seizure event type and the predefined seizure triggering condition; and modify, using the wearable device, an opacity of a transparent surface of the wearable device based at least in part on the seizure event prediction data object.

18. The system of claim 16, wherein the second sub-model is configured to determine the one or more predefined head movement features and the one or more predefined facial movement features based at least in part on a Eulerian video processing technique.

19. The system of claim 15, wherein the one or more processors are further caused to:

provide an indication of the seizure event prediction data object to a user computing entity; and store information associated with the seizure event prediction data object to a user profile.

20. The system of claim 16, wherein the sensor data is captured in real-time by an inertial measurement unit (IMU) of the wearable device.

\* \* \* \* \*

UNITED STATES PATENT AND TRADEMARK OFFICE
CERTIFICATE OF CORRECTION

Page 1 of 1

PATENT NO. : 12,327,637 B2
APPLICATION NO. : 17/451729
DATED : June 10, 2025
INVENTOR(S) : Jon Kevin Muse et al.

It is certified that error appears in the above-identified patent and that said Letters Patent is hereby corrected as shown below:

In the Claims

In Column 29, Line 12, Claim 2, delete "identifying one" and insert -- identifying, by the one or more processors, one --, therefor.
In Column 30, Line 2, Claim 8, delete "remodifying the" and insert -- remodifying, by the one or more processors, the --, therefor.
In Column 30, Line 27, Claim 13, delete "of sensor" and insert -- of the sensor --, therefor.
In Column 30, Line 65, Claim 16, delete "caused" and insert -- configured --, therefor.
In Column 32, Line 22, Claim 19, delete "caused" and insert -- configured --, therefor.

Signed and Sealed this
Ninth Day of September, 2025

Coke Morgan Stewart
*Acting Director of the United States Patent and Trademark Office*